(12) United States Patent
van Dam et al.

(10) Patent No.: US 8,838,203 B2
(45) Date of Patent: Sep. 16, 2014

(54) INVERSE IMAGING OF ELECTRICAL ACTIVITY OF A HEART MUSCLE

(75) Inventors: Peter Michael van Dam, Arnhem (NL); Adriaan Van Oosterom, Linden (NL)

(73) Assignee: Cortius Holding B.V., Amersfoort (NL)

( * ) Notice: Subject to any disclaimer, the term of this patent is extended or adjusted under 35 U.S.C. 154(b) by 142 days.

(21) Appl. No.: 13/380,244

(22) PCT Filed: Jun. 24, 2010

(86) PCT No.: PCT/NL2010/050397
§ 371 (c)(1),
(2), (4) Date: Mar. 12, 2012

(87) PCT Pub. No.: WO2010/151130
PCT Pub. Date: Dec. 29, 2010

(65) Prior Publication Data
US 2012/0157822 A1    Jun. 21, 2012

(30) Foreign Application Priority Data

Jun. 24, 2009    (EP) .................................... 09163688

(51) Int. Cl.
*A61B 5/0205*    (2006.01)
*A61B 5/0402*    (2006.01)
*A61B 18/00*    (2006.01)

(52) U.S. Cl.
CPC ..... *A61B 5/0402* (2013.01); *A61B 2018/00839* (2013.01)
USPC ........... 600/411; 600/407; 600/424; 600/426; 600/523; 600/509; 600/528

(58) Field of Classification Search
CPC .................... A61B 2018/00839; A61B 5/0402
USPC .......... 600/407, 411, 424, 426, 523, 528, 509
See application file for complete search history.

(56) References Cited

U.S. PATENT DOCUMENTS

| 6,990,370 | B1 | 1/2006 | Beatty et al. | |
|---|---|---|---|---|
| 2005/0222515 | A1* | 10/2005 | Polyshchuk et al. | 600/528 |
| 2007/0270703 | A1* | 11/2007 | He et al. | 600/509 |
| 2008/0009758 | A1* | 1/2008 | Voth | 600/523 |
| 2008/0177192 | A1* | 7/2008 | Chen et al. | 600/509 |
| 2008/0234564 | A1* | 9/2008 | Beatty et al. | 600/374 |
| 2010/0179421 | A1* | 7/2010 | Tupin | 600/426 |
| 2010/0274123 | A1* | 10/2010 | Voth | 600/424 |
| 2012/0143030 | A1* | 6/2012 | Harlev et al. | 600/375 |

OTHER PUBLICATIONS

Van Dam: "Simulating ECG Changes During Acute Myocardial Ischemia," Computers in Technology, Jan. 1, 2007 IEEE Computer Society, US, FR, vol. 34t, pp. 325-328, XP002556299.

(Continued)

*Primary Examiner* — Baisakhi Roy
(74) *Attorney, Agent, or Firm* — Waddey & Patterson, P.C.; James R. Cartiglia

(57) ABSTRACT

A method for providing a representation of the distribution, fluctuation and/or movement of electrical activity through heart tissue, said method comprising: obtaining an ECG of the heart comprising said tissue; obtaining a model of the heart geometry; obtaining a model of the torso geometry; relating the measurements per electrode of the ECG to the heart and torso geometry and estimating the distribution, fluctuation and/or movement of electrical activity through heart tissue based upon a fastest route algorithm, shortest path algorithm and/or fast marching algorithm.

22 Claims, 19 Drawing Sheets

(56) References Cited

OTHER PUBLICATIONS

Peter M. Van Dam: "Non-Invasive Imaging of Cardiac Activation and Recovery" Annals of Biomedical Engineering, vol. 37, Sep. 2009 No. 9, pp. 1738-1756 XP002556297.

M. Sermesant et al: "A Fast-Marching Approach to Cardiac Electrophysiology Simulation for MXR Interventional Imaging" MICCAI 2005, LNCS 3750 pp. 507-615 2005 Springer-Verlag Berlin Heidelberg 2005 XP002601160.

IEEEE Engineering in Medicine and Biology: "The Forward and Inverse Problems of Electrocardiography: Gaining a Better Qualitative and Quantitative Understanding of the Heart's Electrical Activity" Sep./Oct. 1998, pp. 85-122 XP000779560.

Peter M. Van Dam et al: "Application of the fastest route algorithm in the interactive simulation of the effect of local ischemia on the ECG" Medical and Biologicl Engineering and Computing Jan. 1, 2009 Springer, Heildelberg, DE, vol. 47, pp. 11-20, XP002556298.

G. Fischer et al: "Computationally Efficient Noninvasive Cardiac Activation Time Imaging" Methods of Information in Medicine, Jan. 1, 2005 Schattauer GmbH, DE, vol. 44, pp. 674-686, XP002556296.

* cited by examiner a b 50 mm/s 10 mm/mV

INVERSE IMAGING OF ELECTRICAL ACTIVITY OF A HEART MUSCLE

The invention relates to methods for providing images of heart tissue, in particular of heart muscles, in particular images that can provide information on different areas of a heart muscle. In particular the invention relates to non-invasive methods of providing information on heart muscles. Furthermore the invention relates to methods for providing such images based upon ECG's and heart torso geometry measurements and/or models.

INTRODUCTION

The biophysical modelling approach used in this application relates the activation and recovery of the heart directly to the electrical processes within the myocardial cells. A proper understanding of the underlying processes within the myocardial cells and the electrical functioning of the whole heart is important for linking the observations on the body surface to the actual activation and recovery of the heart.

At rest, ion pumps in the membrane of the cardiac cell maintain a potential difference over the membrane: the cell is polarised. Electrical stimulation of a cell will influence the ion kinetics at the membrane, which causes the cell to depolarise. This depolarisation initiates the influx of calcium, which in turn elicits the contraction. In order to enable a subsequent contraction the calcium must be removed and the cells brought back to the resting polarised state.

Myocardial cells are electrically coupled by means of gap junctions [1]. This intercellular coupling produces a domino effect, i.e. once a sufficiently large number of cells are depolarised, these cells are able to depolarise their direct neighbours. This process continues until the whole heart is depolarised. The heart has four chambers; two atria and two ventricles (see FIG. 1). The atria have a thin wall and a limited pump function; the ventricles perform the mechanical action involved in pumping the blood to the lungs, other organs, and body tissues.

The activation of the heart starts in the sinus node region, an atrial area close to the vena cava superior [2] (FIG. 1). The sinus node consists of so-called pacemaker cells, which depolarise slowly and autonomously until the depolarisation threshold is reached, resulting in the fast depolarisation of the cells (FIG. 2a). The nervous system controls the heart rate by influencing this slow autonomous depolarisation process. These pacemaker cells activate the atria by means of the intercellular coupling. This coupling is more effective at the far ends of the elongated atrial myocardial cells than on the remaining part of the cell surface [3,4]. These differences in electrical coupling and cell morphology result in an activation wave that propagates faster in the longitudinal direction than in the transverse direction [3,5,6], i.e. the propagation velocity through myocardial tissue is at least partially anisotropic [7].

On a functional level, locally a higher propagation velocity might be expected in areas between right atrium (sinus node) and left atrium to obtain a more synchronous atrial contraction. On the other hand, in a large part of the atria pectinate muscles arise, running criss-cross along the wall [8]. On a larger scale, therefore, the atrial activation might be well approximated by a wave spreading with uniform velocity, similar to Huygens wave propagation [9]. Because of the limited atrial wall thickness, on average less than 2 mm [10], the activation wave procedes approximately parallel to the wall surface, i.e. the endocardium and epicardium are locally activated almost simultaneously [11].

The atrial activation wave finally reaches the atrio-ventricular junction, also called the bundle of His, an area where the atrial myocardium inserts into, but is electrically separated from, the ventricular myocardium [12,13]. The electrical impulse is slowly transmitted by the AV node which moves over into two His bundles through which the impulse is rapidly conducted into the Purkinje system (FIG. 1). The Purkinje system in humans forms a dense network on the lower part of the left and right endocardial wall [14,15], connected to the myocardium at the endings of the Purkinje fibres. This network facilitates the rapid spread of activation, synchronizing the ventricular contraction by means of the activation of ventricular myocardium from multiple sites [16].

Once the ventricular myocardium becomes activated, anisotropic activation propagation plays a major role [1]. As in atrial cells, the electrical coupling of the ventricular cells is most prominent on the far ends. Moreover, ventricular myocardial cells are ordered in bundles running obliquely from apex to base [17,18] (FIG. 1). This bundle structure causes the activation wave to fan out in an elliptic way over the heart surface [19]. Because of this, transmural propagation, from the inner part of the wall, endocardium, to the nearby outer part, epicardium, (wall thickness up to 15 mm) is slower than along the ventricular surface [16].

The activation is followed by the repolarisation of the myocardial cells, in which different stages can be distinguished (FIG. 2b) [20]. In the resting state the transmembrane potential of myocardial cells is maintained at approximately −85 mV. When a cell depolarises (phase 0) the transmembrane potential rises to approximately +15 mV, immediately followed by an early repolarisation (phase 1), a slowly decreasing plateau (phase 2), and finally the recovery (phase 3), during which myocardial cells are brought back to their resting polarised state (phase 4). In FIG. 2b two examples of transmembrane potential waveforms are shown. The major differences in morphology are found in early repolarisation phase (1), resulting in difference in plateau phase amplitude. During the plateau phase the amplitude decreases slowly until the repolarisation phase (3) sets in. The difference between the timing of local activation and recovery (repolarisation) is the local action potential duration (APD).

The contraction of the heart is initiated by the fast electrical depolarisation of the membranes of the cardiac cells. This depolarisation spreads in a wave-like fashion over the heart. Immediately after the depolarisation phase the myocardial cells start to repolarise, initially a relatively slow process, followed some 200 ms later by a faster phase that takes up to 150 ms. These electrical processes within the heart generate currents, which are conducted through the various body tissues. As a result these currents generate potentials on the body surface. Recordings of these potentials are called electrocardiograms or ECGs. Since the early days of Einthoven, more than 100 years ago, the ECG has been recorded systematically. This non-invasive registration method has become a major clinical tool in assessing the (dis)functioning of the heart. However, in clinical practice it is difficult to relate the ECG signals directly to the actual electric activation and recovery processes in the heart. Non-invasive imaging techniques can assist in solving this visualisation problem by mapping and displaying the local activation and recovery times on the surface of the heart.

Numerous studies have been performed to determine the spatial distribution of the action potential duration. Most of these studies used epicardial potentials to estimate the local APD or the closely related activation recovery time [21,22, 23]. According to Franz et al. [24] a negative correlation exists between local activation time and APD, such that sites that depolarise early have a relatively long APD, as the depolarised state of the neighbouring areas keeps the potential within the cell relatively high, thus delaying repolarisation. The opposite effect is found in sites that undergo late activation.

For a single heartbeat the electrical activity of the atria and ventricles can be distinguished in the ECG. The first clear sign in the ECG of electric activity during any heart beat is the P wave (see FIG. 3), resulting from the activation of the atria. This is followed by the QRS complex, signalling the ventricular activation. The recovery of the ventricles is visible in the ECG as the T wave. Atrial repolarisation cannot be observed clearly in this display since the magnitude of the associated current is much smaller than that generating the P wave and part of its timing coincides with that of the much larger QRS complex [25].

The morphology of the ECG is determined by the activation and recovery sequence of the heart. The activation sequence of the human heart has been studied extensively for decennia; invasively [16,26,27,28] as well as non-invasively [29,30,31,32].

The sequence of activation and recovery of the heart, atria and ventricles, has physiological significance and clinical relevance. The standard 12-lead electrocardiogram (ECG), commonly used in diagnostic procedures, provides insufficient information for obtaining an accurate estimate of these sequences in all types of abnormality or disease.

The invention now provides a method for providing a representation of the distribution, fluctuation and/or movement of electrical activity through heart tissue, in particular a heart muscle, said method comprising: obtaining an ECG of said heart tissue; obtaining a model of the heart geometry; obtaining a model of the torso geometry; relating the measurements per electrode of the ECG to the heart and torso geometry, in particular based upon a source model and estimating the distribution, fluctuation and/or movement of electrical activity through the heart muscle based upon a fastest route algorithm, a shortest path algorithm and/or fast marching algorithm or combinations thereof. More detailed estimates of the distribution, fluctuation and/or movement can be obtained by using a cellular automaton or by the ion kinetics model, but these are generally not considered necessary. In areas of heart tissue where the algorithms mentioned do not provide an estimation that matches the measured ECG's sufficiently, combinations of algorithms with cellular automaton and/or the ion kinetics model may be used. These models are typically used for the surfaces (epicardial and endocardial) of the heart tissue. In addition a model has to be assumed for movement through the cardiac wall. A linear model seems suitable, although others may be used, in particular near or at the Purkinje system or in areas where the wall is innervated.

According to the present invention in particular the fastest route algorithm, in particular together with the equivalent double layer model, (vide infra) allows for so-called inverse functional imaging of electrical activity (activation, recovery) of a heart muscle, in particular of a complete image of a heart, as well as particular areas of interest both on the outside (epicardium) and inside (endocardium) of the heart or both. As an algorithm that may lead to comparable results as the fastest route algorithm, the fast marching algorithm, the shortest path algorithm, the ion kinetic model or the cellular automaton model may be used.

An ECG is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the movement of the electrical activity has to be provided. According to the invention preferably the fastest route algorithm (vide infra) is used to make such an estimate. For certain areas of the heart the shortest path algorithm may suffice, but for an accurate estimate for all areas of the heart, corrections (particularly for anisotropy) need to be made, which can be done by the fastest route algorithm. No single individual is the same. In order to correct for the differences in size, shape and composition of the heart and the torso (which will influence the measured signals in the ECG (at the body surface) of an individual, a model of said heart and torso is required. Such a model can be obtained from (MRI) measurements, but as more and more of such measurements become available (parts of) these measurements may be omitted and taken from a reference database. The functional images provided by the present invention are provided in silico and preferably depicted on a computer screen, allowing for inter alia virtual "3D" representations. Clinically it may be very relevant which part of a heart muscle is not functioning properly. Although based on present day technology some distinctions are possible, the present invention allows for enhanced localisation of activation and/or repolarisation (recovery) disorders, as well as the identification of areas affected by insults, trauma or otherwise. Thus in one embodiment the invention provides a method according to the invention whereby the representation is an estimation of the activation of different areas of the heart muscle. For these images it may not be necessary to provide an image of a complete heart, although this is preferred according to the present invention.

As stated above some model of the torso and heart of an individual is required in order to calculate electrical patterns based on ECG's. Such a model can be obtained through MRI measurements, but any measurement providing information on shape, size and composition of torso and heart is applicable. Alternatives for MRI are Echi, Röntgen, CT-scan, PET-scan and photo/video (thorax only with electrode positions) measurements. However MRI measurements are preferred. Thus in another embodiment the invention provides a method according to the invention, whereby the heart- and/or the torso geometry is based upon a measurement by MRI.

The present invention allows for providing functional images of electrical activity as it moves through the heart muscle, both activation and repolarisation (recovery) can be visualised and have been shown to match the actual physiological electrical activity patterns of the actual heart. Recovery has clinical relevance on its own, thus the invention provides in yet another embodiment a method according to the invention, whereby repolarisation (recovery) of areas of the heart muscle is estimated based upon the sequence of activation through the heart muscle. The imaging methods according to the invention are capable of revealing e.g. repolarisation dispersion. Great dispersion in repolarisation times means that a next activation wave over the heart muscle may encounter cells that are not yet repolarised and therefore cannot be activated. This often leads to arrhythmia. The present invention can therefore detect whether the heart of a subject is prone to go into arrhythmia. It can also be used to determine the effects of substances given to suppress, prevent or end arrhythmic events. As stated herein before, the methods according to the invention preferably employ the fastest route algorithm. Preferably this algorithm is adjusted for anisotropy in the heart muscle. This allows for correction of the image for bundles of fibers and start of activation at multiple foci. It also allows for correction of the electrical signal travelling faster in certain directions than in others (fibre orientation). Thus the present invention provides a method according to the invention, further comprising adjusting the activation estimation by estimating the fiber orientation in at least one area of the heart muscle. The methods according to the invention thus can identify additional activation foci whether they are epicardial or endocardial. It may thereby serve as a guide for surgical procedures intended to remove such additional foci (ablation). On the other hand it may guide procedures where additional activation sites have to be created. It is particularly helpful that the present invention distinguishes epicard and endocard, since different procedures may need to be used to reach epicardial or endocardial sites.

In order to further fine tune the estimated images according to the invention, the invention provides a method whereby the speed, activation and/or recovery estimation is optimised by a Levenberg-Marquardt method.

The preferred source model according to the invention is the so-called equivalent double layer model (EDL), vide infra. Although this model is preferred deviations (in particular improvements) of this model may be possible. An ion-kinetic model may be suitable, but is more cumbersome to work with. More simple, but less accurate would be the so-called moving dipoles model.

Thus in a further embodiment the invention provides a method according to the invention, wherein the source model is an equivalent double layer model. A further layer of information on electrical activity (in at least part) of a heart muscle is available with the methods and means according to the invention. Thus in a further embodiment the invention provides a method according to the invention, wherein the amplitude of a local transmembrane potential in a heart muscle is estimated based on the ST segment of an ECG of said heart muscle. The heart-torso model obtained preferably by MRI in a preferred embodiment is a volume conductor model. Thus in a further preferred embodiment the invention provides a method according to the invention, wherein a volume conductor model of the heart- and/or torso geometry is provided. A preferred volume conductor model is disclosed in international application PCT/NL2009/050711, published in May 2010). Preferably the volume conductor model is adjusted based upon a database of various heart—and/or torso geometries. It is also preferred to improve estimates relating to a source model by adjustments based upon a database of various heart geometries. The databases mentioned herein are of course computer readable databases on data carriers within or outside computers. The invention also provides a computer provided with—means (direct or indirect) of providing torso/heart geometries, —means to (directly or indirectly) provide ECG measurements and a program (software) to convert these measurements to an image of electrical activity in a heart muscle presentable on a computer screen or other presenting medium.

The methods and means according to the invention can be used in a hospital setting, but, in particular with mobile data transfer technology, can also be used to monitor a patient from a distance. Once a torso/heart geometry estimate is available the ECG measurements can be made with a device that can be worn by a subject and the recordings can be transmitted to a computer on which the other necessary data and software is present. Thus the invention provides singular, plural, as well as continuous measurements and thereby both historical and "real time" images.

The methods and means according to the invention can also be used to measure and/or envisage effects for the heart resulting from any outside influence on the body of a subject.

Physical exertion of the subject may be such an influence as well as stress, etc. Particularly of interest are the effects of chemical/biological substances that are introduced into subjects. Particularly substances that are intended for the treatment of subjects for a certain disease.

Thus the invention provides a method for determining the effects of a substance on at least one area of a heart muscle, comprising obtaining a first and at least one further representation of a heart muscle according to the invention, whereby said first representation is obtained from a heart not exposed to said substance and said at least one further representation is obtained during and/or after exposure of said heart to said substance. Again, these measurements can be taken several times or even continuously. Such substances may be intended to treat heart disease, but also to treat other diseases, or be considered for human uptake (food/nutrients/cosmetics, pollutants, etc.) of which it is desired to know possible toxicity for the heart upon such uptake. Different areas of the heart may be affected differently by such substances and the relevance of different areas may also differ. In a preferred embodiment the invention thus provides a method according to the invention whereby different areas of a heart muscle are analyzed for effects of said substance.

DETAILED DESCRIPTION OF THE INVENTION

Since the inception of electrocardiography [33,34] several methods have been developed aimed at providing more information about cardiac electric activity on the basis of potentials observed on the body surface. The differences between these methods relate to the implied physical description of the equivalent generator representing the observed potential field. The earliest of these are the electric current dipole, a key element in vectorcardiography [35,36] and the multipole expansion [37]. Neither of these source models offer a direct view on the timing of myocardial activation and recovery, or other electro-physiologically-tinted features.

From the 1970s onwards, the potential of two other types of source descriptions have been explored [38,39]. This development stemmed from increased insight in cardiac electro-physiology and advances in numerical methods and their implementation in ever more powerful computer systems. The results of both methods are scalar functions on a surface. The solving of the implied inverse problem may, accordingly, be viewed as a type of functional imaging, which has led to their characterisation as, e.g., "Noninvasive Electrocardiographic Imaging (ECGI)" [40] or "Myocardial Activation Imaging" [41]. A brief characterisation of both methods is as follows.

The first surface source model is that of the potential distribution on a closed surface closely surrounding the heart, somewhat like the pericardium, referred to here as the pericardial potential source (PPS) model. The model is based on the fact that, barring all modelling and instrumentation errors, a unique relation exists between the potentials on either of two nested surfaces, one being the body surface, the other the pericardium, provided that there are no active electric sources in the region in between. It was first proposed at Duke by Martin and Pilkington [42]; its potential has subsequently been developed by several other groups, e.g., [43,44,45,46, 47].

The second type of surface source model evolved from the classic model of the double layer as an equivalent source of the currents generated at the cellular membrane during depolarisation, described by Wilson et al. [48]. Initially, this current dipole layer model was used to describe the activity at the front of a depolarisation wave propagating through the myocardium [49,50]. Later, Salu [51] expressed the equivalence between the double layer at the wave front and a uniform double layer at the depolarised part of the surface bounding the myocardium, based on solid angle theory [52]. This source description has been explored by others, e.g., [31,41,53,54,55].

This application describes recent progress made in inverse procedures based on the second type of surface source model: the equivalent double layer on the heart's surface as a model of the electric sources throughout the myocardium; we refer to it as the EDL model. In contrast with the PPS model, the EDL source model relates to the entire surface bounding the atrial or ventricular myocardium: epicardium, endocardium and their connection at the base. As mentioned in the previous paragraph, the EDL was initially used for modelling the currents at the depolarizing wave front only. Based on the theory proposed by Geselowitz [56,57], it was found to be also highly effective for describing the cardiac generator during recovery (the repolarisation phase of the myocytes). The transmembrane potentials (TMPs) of myocytes close to the heart's surface act as the local source strength of the double layer. Several examples of its effectiveness in forward simulations have appeared in the literature [58,59,60,61]. A description of the model in inverse procedures is seen in the paper by Modre et al. [62], dedicated to the atrial activation sequence. In our application the TMPs' wave forms were specified by an analytical function involving just two parameters, markers for the timing of local depolarisation and repolarisation. These parameters were found by using a standard parameter estimation method, minimizing the difference between observed body surface potentials (BSPs) and those based on the source description. Since the body surface potentials depend non-linearly on these parameters, a non-linear parameter estimation technique is required, which demands the specification of initial estimates. It is here that some novel elements are reported on, and a major part of this application is devoted to their handling. The initial parameters for the timing of local depolarisation were typically based on the fastest route algorithm, taking into account global properties of anisotropic propagation inside the myocardium. Those pertaining to recovery were based on electrotonic interaction as being the driving force for the spatial differences in the local activation-recovery interval.

In the Methods section, the entire inverse procedure is described and a justification given of those model parameters that are treated as constants during the optimisation procedure. In the Results section, examples of inverse estimated ventricular activation and recovery sequences are presented: those of a healthy subject, a WPW patient and a Brugada patient during an Ajmaline provocation test. The value, application and limitations of this approach are considered in the Discussion.

For the situation in which the electrical activity of the heart is defined, the potentials on the body surface can be simulated. This procedure is known as the forward problem in electrocardiography [63]. To obtain a solution to the inverse problem the electrical activity of the heart needs to be related to measured ECG signals on the body surface [39]. Clearly the non-invasive method of cardiac activation and recovery times is of physiological and clinical relevance. Any solution method to such inverse problem requires a solution to the associated forward problem.

In order to solve the forward problem, one needs to compute the potential differences at the body surface that result from the electric currents generated by the heart. For this purpose a realistic description of the volume conductor is needed, incorporating the shape and conductivities of the relevant tissues. The standard procedure to obtain such a volume conductor model is to detect the contours of the relevant tissues in a set of MR images of the subject involved and reconstruct triangulated computer models of these tissues [64,65,66,67]. Based on earlier research regarding the simulation of the QRS complex [66,68], we have chosen to include in our volume conductor model the blood filled cavities within the heart, the lungs, and the rest of the torso with conductivity values 0.6 S/m, 0.04 S/m and 0.2 S/m respectively. We have used the boundary element method to compute the transfer function based on the specified volume conductor model for relating the source activity to the potentials at the body surface. Due to the large number of cardiac cells in the human heart (approximately $10^{10}$) a computer model is typically not able to simulate the activity of all these cells nor can the full complexity of all interactions between ionic currents be incorporated. Any non-invasive imaging method therefore needs to postulate a source model, representing the electrical activity of the heart. The earliest of these is the electric current dipole, a key element in vectorcardiography [35,36], and the multipole expansion [37]. Neither of these source models offer a direct view on the timing of myocardial activation and recovery, or other electro-physiologically related features. From the 1970s onwards, the potential of two other types of source descriptions have been explored. This development followed from an increased insight into cardiac electrophysiology. The results of both methods use source descriptions at the surface of the heart. Solving the implied inverse problem may accordingly be viewed as a type of functional imaging, which has led to their characterisation as, e.g., "Non-invasive Electrocardiographic Imaging (ECGI)" [40] or "Myocardial Activation Imaging" [41].

There is a serious complication involved in the use of both models: the associated inverse problem is ill-posed, i.e. small deviations in the measured ECG data may result in completely different outcomes of activation and recovery times [39]. A solution to the inverse problem can therefore only be obtained through regularisation of the source parameters such that these parameters express desired properties. A brief characterisation of both methods is as follows.

The first distributed surface source model is that of the potential distribution on a surface closely surrounding the heart, somewhat like the pericardium, referred to here as the pericardial potential source (PPS) model. The model is based on the fact that, barring all modelling and instrumentation errors, a unique relation exists between the potentials on either of two nested surfaces, one being the body surface, the other the pericardium, provided that there are no active electric sources in the region in-between. It was first proposed at Duke [42]; its potential has subsequently been developed by several other groups, e.g., [43,44,46,47,69].

The second model, used in our research, is based on the macroscopic equivalent double layer (EDL) model [70], applicable to the entire electrical activity of the atria and ventricles, at any time instant [71]. This source model stems from the classic model of the double layer as an equivalent source of the currents generated at the cellular membrane during depolarisation, described by Wilson et al. [48]. Initially, this current dipole layer model was used to describe the activity at the front of a depolarisation wave propagating through the myocardium [49,50]. Later, Salu [51] expressed the equivalence between the double layer at the wave front and a uniform double layer at the depolarised part of the surface bounding the myocardium, based on solid angle theory [52] (see FIG. 4).

More recently, Geselowitz [56,57] has shown, using a bidomain model, that the actual current source distribution within the heart is equivalent to a double layer at the surface of the myocardium with a strength proportional to the local transmembrane potential (TMP) [72]. The waveform of the transmembrane potential at each location on the myocardial surface is described by two parameters: the local activation and recovery time. Consequently, the source parameters consist of the activation and recovery times. The relation between the source parameters and the source strength is a non-linear relation.

In a previous study by Huiskamp et al. [73] the initial activation times were estimated from the time integral of the measured QRS complex. Another initial estimate, introduced by Huiskamp and Greensite, is based on the critical point theorem [29,41,74]. Both initialisation methods, however, lack a direct link to the electrophysiology of the heart.

An initial estimate for the atrial or ventricular activation can be obtained based on the propagation of the electrical activation inside the myocardium. In our application, for multiple activation sequences produced based on a propagation model the corresponding ECGs are computed. The activation sequence whose computed ECG matches the actual ECG the best is used as the initial estimate.

As mentioned before, the activation of myocardial tissue in the healthy human heart is initiated by the sinus node in the atria and by the His-Purkinje system in the ventricles. In pathological cases, as may be encountered in a clinical setting, the initiation may occur anywhere within the atria or ventricles. These electrophysiological and clinical facts require the activation modelling to be able to combine activation sequences originating from multiple locations (foci), e.g. as is the case for the His-Purkinje initiated activation. Furthermore, the method has to be able to determine the location of a focus anywhere in the atria or ventricles.

Several sophisticated models are available to simulate cardiac activation [59,75,76,77,78]. However, most of these models require many hours to compute a single activation sequence. These models cannot be used in the inverse procedure, because of the vast number of activation sequences that needs to be tested. An approach that is able to simulate an activation sequence within a second is a cellular automaton model [79,80]. These cellular automaton models involve that a volume description of the myocardium is required instead of the surface description used in our approach. The latter used the fastest-route algorithm, based on the shortest path algorithm [81,82], while using a surface description of the heart only.

The shortest path algorithm, was designed by Dijkstra to compute the path with minimal length between any two nodes in a graph [83]. A well-known application is the route planning algorithm in any car navigation system, with the roads representing the graph. The applications and implementation issues of the fastest-route algorithm in modelling cardiac activation for the application of finding an initial estimate in the inverse procedure are the main topics of interest of this application.

The simulation of ECG signals generated by atrial activity, and consequently the non-invasive estimation of atrial activation, requires a realistic volume conductor model. In a preliminary study, the influence of certain inhomogeneities within the thorax (lungs and the intra-cardiac blood volume) in the forward simulation of the body surface potentials generated by atrial electric activity is studied [84].

In good approximation, atrial activation can be compared to a Huygens wave spreading with uniform velocity in all directions. The first application of the shortest path algorithm (SPA), assuming uniform velocity, was therefore applied to generate atrial activation sequences [85]. To keep the setup as simple as possible atrial wall thickness was discarded, revealing the concept of prominent routes. Such routes show the intensity in which of the atrial nodes are utilised in the various atrial paths generated by the shortest path algorithm.

Within the ventricles anisotropic propagation is known to play a prominent role. Consequently it has to be incorporated in the application of SPA to generate ventricular activation sequences. In the fastest route algorithm (FRA), which is based on the SPA, is introduced. In the FRA, inhomogeneous propagation velocities within the ventricles can be incorporated. The FRA is used to simulate the effect a local reduction of the propagation velocity on the overall activation sequence and the simulated ECG.

1.1 Materials

The results shown in this application are based on data recorded in three subjects. The nature of this data is summarised below. More details can be found in previous publications [29,64,85,86], in which essentially the same material was used.

In each patient, a 64-lead ECG was recorded. Of course more leads (up to a point) may provide higher resolution. Typically beyond 200 leads the increase in resolution does not justify the addition of leads. Also less leads may be used, particularly when more database information can be incorporated. Less than the standard 12 leads may lead to results with limited resolution. For each subject, MRI-based geometry data was available from which individualised numerical volume conductor models were constructed, incorporating the major inhomogeneities in the conductive properties of the thorax, i.e. the lungs, the blood-filled cavities and the myocardium.

The first subject (NH) is a healthy subject [85]. This subject was included to illustrate intermediate and final results of the described inverse procedure. The other two subjects are added to illustrate clinical applications. The second subject (WPW) is a WPW patient for whom previously estimated activation times have been published [29,64]. The recorded ECGs included episodes in which the QRS displayed the typical WPW pattern, i.e., a fusion beat in which the activation is initiated at both the AV node and the Kent bundle. The location of the latter was determined invasively. The ECGs were also recorded after an AV-nodal block had been induced by a bolus administration of adenosine, resulting in an activation sequence solely originating from the Kent bundle.

The third case was a Brugada patient in whom ECG data were recorded during infusion of a sodium channel blocker (Ajmaline) [86], 10 bolus infusions of 10 mg, administered at one-minute intervals [87], which changes the activation and/ or recovery sequence. The beats selected for analysis were: the baseline beat 5 minutes prior to infusion and the beat after the last bolus had been administered.

For each subject, the number of nodes representing the numerical representation of the closed surface (endo- and epicardium) of the ventricles and the observed QRS durations are listed in Table 1.

TABLE 1

Subjects for whom the ventricular depolarisation and repolarisation sequences were estimated.

| Subject | Type | # nodes on the heart's surface | QRS duration ms |
|---|---|---|---|
| WPW | WPW patient | 697 | 119 (fusion beat) |
|  |  |  | 159 (AV blocked) |
| BG | Brugada patient | 287 | 104 (baseline) |
|  |  |  | 124 (peak infusion) |
| NH | Healthy subject | 1500 | 101 |

For subject WPW the fusion beat data and after the administration of adenosine to block the AV node. For subject BG the baseline beat data (first row) and after the last administration of Ajmaline are given.

1.2 Methods
1.2.1 Local EDL Strength

The time course of the TMP acting as the local EDL source strength was specified by the product of three logistic functions, the functions of the type $$L(t; \tau, \beta) = \frac{1}{1 + e^{-\beta(t-\tau)}}. \tag{1}$$

describing a sigmoidal curve with maximum slope $\beta/4$ at $t=\tau$. The first of these functions described phase (0) of the TMP time course [20], the depolarisation phase, as $$D(t;\delta) = L(t;\delta,\beta), \tag{2}$$

with $\delta$ the timing of local depolarisation and the factor $\beta$ setting the steepness of the upstroke.

Local repolarisation refers to the period during which the TMP moves toward its resting state (Phases 3 and 4), a process that may take up to some hundred ms. The TMP wave form during this period was described as $$R(t;\rho) = L(t;\rho,\beta_1)L(t;\rho,\beta_2), \tag{3}$$

in which $\rho$ sets the position of the inflection point of the TMP's down slope and $\beta_1$ and $\beta_2$ are constants setting its leading and trailing slope. Note that the action potential duration, $\alpha$, defined as $$\alpha = \rho - \delta, \tag{4}$$

represents the time interval between the marker used for the timing of local repolarisation $\rho$ and the timing of local depolarisation $\delta$; it may be interpreted as the activation recovery interval [88].

In summary, the waveform specifying the strength $S(t;\delta,\rho)$ of the local EDL was $$S(t;\delta,\rho) = D(t;\delta)R(t;\rho). \tag{5}$$

Note that this function depends on two parameters only. The constants $\beta_1$ and $\beta_2$ were found by fitting $S(t;\delta,\rho)$ to the STT segment of the rms(t) curve of the 64 ECGs of the individual subjects, as is described in [61] and motivated in [89]. Examples of the TMP wave forms obtained from (5) are shown in FIG. 5. These may be shifted in time as appropriate in individual cases. Moreover they may be scaled in amplitude to an arbitrary, uniform level in the application to non-ischemic tissue for which, based on solid angle theory applied to a closed double layer, a uniform strength produces no external field.

1.2.2 Computing Body Surface Potentials

Based on the EDL source description, with its local strength at position $\vec{x}$ on the surface of the ventricular myocardium ($S_v$) taken to be the local transmembrane potential $V_m(t,\vec{x})$, the potential $\phi(t,\vec{y})$ generated at any location $\vec{y}$ on the body surface is $$\phi(t,\vec{y}) = \int_{S_v} B(\vec{y},\vec{x}) V_m(t,\vec{x}) d\omega(\vec{y},\vec{x}), \tag{6}$$

in which $d\omega(\vec{y},\vec{x})$ is the solid angle subtended at $\vec{y}$ by the surface element $dS(\vec{x})$ of $S_v$, and $B(\vec{y},\vec{x})$ is the transfer function expressing the full complexity of the volume conductor (geometry and tissue conductivity). Previous studies [31,70] indicated that an appropriate volume conductor model requires the incorporation of the heart, blood cavities, lungs and thorax. In this study, the conductivity values $\sigma$ assigned to the individual compartments were: thorax and ventricular muscle: 0.2 S/m, lungs: 0.04 S/m and blood cavities: 0.6 S/m.

The complex shape of the individual compartments within the volume conductor model does not permit one to determine $B(\vec{y},\vec{x})$ by means of an analytical method. Instead, numerical methods have to be used. In this study we used the boundary element method (BEM) [38,90]. Another suitable method may be the Finite element method (FEM). By means of the BEM, while using formula (5) for describing the TMP, the potential at any node l of the discretised (triangulated) body surface was computed as $$\phi(t,\ell) = \sum_n B(\ell, n) S(t; \delta_n, \rho_n), \tag{7}$$

with n the number of nodes of the triangulated version of $S_v$. For each moment in time this amounts to the pre-multiplication of the instantaneous column vector (source) S by a (transfer) matrix B, which incorporates the solid angles subtended by source elements as viewed from the nodes of the triangulated surface, scaled by the relative jump in $(\sigma_i^+ - \sigma_i^-)/(\sigma_i^+ + \sigma_i^-)$ of the local conductivity values $\sigma_i^+$ and $\sigma_i^-$ at either sides of the interfaces i considered [38,90].

1.2.3 Inverse Computation of Activation and Recovery

The timing of local depolarisation and repolarisation was treated as a parameter estimation problem, carried out by minimizing in the least squares sense with respect to the parameters $\delta$ and $\rho$, the difference between the potentials computed on the basis of (7) and the corresponding body surface potentials V(t,l) observed in the subjects studied. Since the source strength depends non-linearly on the parameters, the minimisation procedure needs to be carried out iteratively, for which we used a dedicated version of the Levenberg-Marquardt algorithm [91] The subsequent steps of this procedure alternated between updating the $\delta$ and $\rho$ estimates. Updating $\delta$ was carried out on the basis of solving $$\arg\min_\delta(\|V - \Phi(\delta;\rho)\|_F^2 + \mu^2\|L\delta\|_F^2). \tag{8}$$

Matrix L represents a numerical form of the surface Laplacian operator [92], which serves to regularise the solution by guarding its (spatial) smoothness, $\mu^2$ its weight [31] in the optimisation process and $\|\ \|_F^2$ the square of the Frobenius norm. Matrix L is the Laplacian operator normalized by the surface [31]. Consequently $L\delta$ is proportional to the reciprocal of the propagation velocity. As the propagation velocity of activation and recovery are in the same order of magnitude the same value for $\mu$ can be used for activation and recovery.

Updating $\rho$ was based on the same expression after interchanging $\delta$ and $\rho$ in the regularisation operator (latter part of (8)). Since the problem in hand is non-linear, initial estimates are required for both. In previous studies, related to the activation sequence (δ) only, the initial estimates involved were derived exclusively from the observed BSPs [31,53,54,55]. The method employed here is based on the general properties of a propagating wave front. From this initial estimate for depolarisation, an estimate of the initial values of the repolarisation marker, ρ, is worked out by including the effect of electrotonic interaction on the repolarisation process.

1.2.4 The Initial Estimate of the Timing of Activation

During activation of the myocardium, current flows from the intracellular space of the depolarised myocytes to the intracellular space of any of its neighbours that are still at rest (polarised at their resting potential). The activation of the latter takes about 1 ms and is confined to about 2 mm. The boundary of this region (the activation wave front) propagates toward the tissue at rest until all of the myocardium has been activated. The propagation can be likened to the Huygens process. The local wave front propagates in directions dominated by the orientation of local fibres, at velocities ranging from 0.3 m/s across fibres to 1 m/s along fibres. Under normal circumstances, ventricular depolarisation originates from the bundle of His, progresses through the Purkinje system, from which the myocardium is activated [93]. In humans this Purkinje system is mainly located on the lower ⅔ of the endocardial wall [14,15]. In other cases, ventricular activation originates from an ectopic focus or from a combination of the activity of the His-Purkinje system and an ectopic focus. The initial estimate of the inverse procedure was based on the identification of one or more sites of initial activation, from which activation propagates. This includes normal activation of the myocardium, which can be interpreted as originating from several foci representing the endpoints of the Purkinje system. The activation sequence resulting from a single focus was derived by using the fastest route algorithm.

1.2.4.1 The Fastest Route Algorithm

The fastest route algorithm (FRA) determines the fastest route between any pair of nodes of a fully connected graph [94]. The term 'fully connected' signifies that all nodes of the graph may be reached from any of the other ones by travelling along line segments, called edges, that directly connect pairs of nodes. In the current application the term edges not only refers to the edges of the triangles constituting the numerical representation of $S_v$, but also to the paths connecting epicardial and endocardial nodes [95], provided that the straight line connecting them lies entirely within the interior of $S_v$.

The structure of the graph is represented by the so-called adjacency matrix, A, which has elements $a_{ij}=1$ if nodes i and j are connected by an edge, otherwise $a_{ij}=0$. By specifying velocity $v_{ij}$ for every edge (i,j), i.e., for every non-zero element of A, the travel time $t_{ij}$ along the edge is $$t_{i,j} = \frac{d_{i,j}}{v_{i,j}}, \tag{9}$$

in which $d_{ij}$ is the distance along the edge.

1.2.4.2 Edge Velocities

In the MRI based geometry of the ventricles the node distances $d_{i,j}$ are known. In the application of (9), the velocities along the edges need to be specified. For want of proper estimates on the myocardial penetration sites of the Purkinje system of the individual subjects, as will be case in the ultimate, clinical application of the proposed method, relatively crude edge velocity estimates were used. Values reported for the anisotropy ratio $v_l/v_t$ of longitudinal and transverse-fiber velocities show a wide range: from 2 to 6 [3,96,97,98].

In this study two related velocities were used: the velocity in directions along the ventricular surface and the one in directions normal to the local surface, $v_l$ and $v_t$, respectively. Their ratio was taken to be 2, the lower end of the range, selected in order to account for transmural rotation of the fibers [18]. For transmural edges that were not normal to the local surface, the travel time $t_{i,j}$ was taken to be $$t_{i,j} = \sqrt{\frac{d^2}{v_l^2} + \frac{h^2}{v_t^2}} = \frac{1}{v_\ell}\sqrt{d^2 + 4h^2}, \tag{10}$$

with d and h the lengths of the projections of the edge along $S_v$ and normal to it, respectively. This procedure approximates locally elliptical wave fronts. The factor 4 appearing on the right in (10) results from the assumed anisotropy ratio 2. Infinite travel times are assigned to pairs (i,j) that are not connected by an edge. The entire set of $t_{i,j}$ constitutes a square, symmetric matrix $A_T$, on the basis of which the FRA computes the shortest travel time between arbitrary node pairs. The results form a square, symmetric travel time matrix T.

1.2.4.3 The Initial Activation Estimate: Multi-Foci Search

The element j of any row i of matrix T was interpreted as the activation time at node j resulting from focal activity at node i only. A search algorithm was designed, aimed at identifying one focus, or a number of foci, which identified the activation sequence yielding simulated body surface potentials that most closely resemble the recorded ones. If a focus at node i is taken to be activated at time $t_i$, the other nodes will be depolarised at $δ_j=t_i+t_{i,j}$. If multiple foci are considered, the activation sequence is computed by the "first come, first served" principle: if K foci are involved, the depolarisation time $δ_j$ is taken to be $$δ_j=\min_k(t_k+t_{k,j}), k=1\ldots K. \tag{11}$$

As is shown on the righthand side of (10), $v_t$ scales the elements of T, and consequently of δ. At each step the intermediate activation sequence, δ, $v_t$ was approximated by max (δ)/$T_{QRS}$, with $T_{QRS}$ the QRS duration (see Table 1). For nodes known to represent myocardial tissue without Purkinje fibers the maximum velocity was set at 0.8 m/s. No maximum velocity was defined for nodes in a region potentially containing Purkinje fibers, the nodes in the lower ⅔ of the endocardial surfaces of the left and right ventricles.

For any activation sequences δ tested, ECGs were computed from (7) at each of the 65 electrode positions (64 lead signals+reference). Note that, with pre-computed matrices B and T, this requires merely the multiplication of the source vector by matrix B. The linear correlation coefficient R between all elements of the simulated data matrix Φ and those of the matrix of the measured ECGs, v, was taken as a measure for the suitability of δ for serving as an initial estimate. The lead signals were restricted to those pertaining to the QRS interval (about 100 samples spaced at 1 ms).

When taking a single node i of the N nodes on $S_v$ as a focus, this results in N basic activation sequences $δ_i$, i=1 ... N, and corresponding values $R_i$. The node exhibiting the maximum R value was selected as a focus.

The entire procedure was carried out iteratively. During the first iteration, the value $t_i=0$ was used, corresponding to the timing of onset QRS. In any subsequent iteration k, the accepted values for $t_i$ were set at 90% of their activation times found from the previous iteration. For the nodes corresponding to the above described 'Purkinje system' the values for $t_i$ were set at 40% of the previous activation times. The Purkinje systems is largely insulated from the myocardial tissue. The propagation velocity in this system ranges between 2 and 4 m/s. The 40% value of $t_r$ represents a 2.5 times higher velocity than the one used in the previous activation sequence, which is usually around 1 m/s. Within the myocardium the differences in velocity are much smaller, limited to approximately 0.7-1 m/s.

Note that a focus can be selected more than once, in which case its activation time decreases. The iteration process, identifying a focus at each step, was continued until the observed maximum value of R decreased.

1.2.5 The Initial Estimate of the Timing of Recovery
1.2.5.1 Background In contrast to the situation during the activation of the myocardium, local recovery may take up to some hundred ms, while the repolarisation process starts almost directly after the local depolarisation. Similar to the situation during activation, throughout the recovery period current flows from the myocytes to their neighbours. The spatial distribution of these currents is not confined to some "repolarisation" boundary, but instead is present throughout all regions that are "recovering". Even so, some measure of the timing of local recovery at node n can be introduced, such as the marker $\rho_n$ introduced previously, and its distribution over $S_v$ can be used to quantify the timing of the overall recovery process.

The intracellular current flowing toward a myocyte is positive when originating from neighbours that are at a less advance state of recovery, thus retarding the local repolarisation stemming from ion kinetics. Conversely, the current flows away when originating from neighbours at a more advanced stage of recovery, thus advancing local repolarisation. The size of the two domains determines the balance of these currents, and thus the magnitude of the electrotonic interaction. At a site where depolarisation is initiated, the balance is positive, resulting locally in longer action potential durations than those at locations where depolarisation ends. The extent of the two domains is determined by the location of the initial sites of depolarisation and overall tissue geometry [99]. As a consequence, local action potential duration, a, is a function of the timing of local depolarisation and, expressed in the notation of (4), so is $\rho(\delta)=\delta+\alpha(\delta)$. Literature reports on the nature of the function $\alpha(\delta)$ as observed through invasive measurements are scarce. In some reports [22,24] a linear function was suggested, for which a slope of –1.32 was reported. The function used in our study involved the subtraction of two exponential functions. For small distances between a local depolarisation (its source) and local ending of activation (its sink) this function becomes linear in approximation [99].

1.2.5.2 The Initial Recovery Estimate

The initial estimate for $\rho$ was found from $\rho(\delta)=\delta+\alpha(\delta)$, with $\delta$ the initial estimate of the timing of depolarisation. The value of $\alpha_n$ at any node n was computed as $$\alpha_n = \bar{\alpha} + \kappa_n(e^{-x_n/\xi} - e^{(1-x_n)/\xi}), \quad (12)$$

with $\bar{\alpha}$ expressing the mean activation recovery interval, $\kappa_n = \hat{\delta}_n - \check{\delta}_n$ the difference between the depolarisation times of the closest sink and source, $x_n = (\delta_n - \check{\delta}_n)\kappa_n$ and $\xi$ a dimensionless shape constant [99]. Sources and sinks of activation were identified as nodes of $S_v$ for which all neighbors in a surrounding region of 2 cm were activated earlier or later, respectively. If more than one source and sink was found within a distance of 4 cm, the average value of the parameters $x_n$ and $\kappa_n$ was assigned to the node n involved. The value of $\bar{\alpha}$ was found through lining up $\bar{\rho} = \bar{\delta} + \bar{\alpha}$ with the apex of the rms(t) signal of the observed ECG signals [100].

1.2.6 Notations/Quality Measures

All lower case bold variables denote vectors, all upper case bold variables refer to matrixes. The differences between simulated and recorded potential data are quantified by using the rd measure: the root mean square value of all matrix elements involved relative to those of the recorded data. In addition, the linear correlation coefficient R between all elements of simulated and reference data are used.

1.3 Results

The differences between simulated and recorded potential data are quantified by using the rd measure: the root mean square value of all matrix elements involved relative to those of the recorded data. In addition, the linear correlation coefficient R between all elements of simulated and reference data is used.

1.3.1 Healthy Subject

For all three cases considered, the weight parameter of the regularisation operator, $\mu$ (see (8)), was empirically determined and set to $1.5 \cdot 10^{-4}$, both while optimizing activation and recovery.

The upstroke slope, $\beta$ (see (1)), was set to 2, resulting in an upstroke slope of 50 mV/ms. The parameter $\xi$ (12) was tuned such that, for the healthy subject (NH), the linear slope of $\alpha(\delta)$ was –1.32 (see Franz et al. [24]). This resulted in a value of $7.9 \cdot 10^{-3}$ for $\xi$.

The initial activation estimated by means of the focal search algorithm is shown in FIG. 6a. In total 7 foci were found in four regions, the first one in the mid-left septal wall, the next on the lower right septal wall and some additional ones on the left and right lateral wall. The result obtained from the non-linear optimisation procedure based on this initial estimate is shown in FIG. 6b.

The initial estimated activation recovery intervals (ARI), derived from the initial activation sequence (FIG. 6a) and the use of equation (12) are shown in FIG. 7a. Note that areas activated early indeed have a longer ARI than the areas activated late. After optimisation (FIG. 7b) the global pattern is similar to the initial one, with a minimally reduced range (from 182-320 ms to 176-300, see also Table 3). This can also be observed in FIG. 8, in which the local initial and final ARI values are plotted as a function of activation time. Consequently, the accompanying reduction in the linear regression slope between initial and estimated ARIs and activation times is also smaller (Table 3). The average of the estimated ARIs is 7 ms shorter than the initial ARIs. In general the estimated ARI values in the right ventricle shorten more compared to the initial estimate whereas the ARI values in the left ventricle and septum prolong slightly (FIG. 8).

The resulting recovery times show very little dispersion (49 ms, Table 3). The right ventricle starts to repolarise first, whereas the (left) septum repolarises last (FIG. 9). Both the left and right ventricle show a prevailing epi- to endocardial direction of recovery.

The measured ECGs and the simulated ECGs based on the estimated activation and recovery times, match very well during both the QRS and the STT segment (see FIG. 10), as indicated by the small rd value (0.12, Table 1).

1.3.2 Fusion Beat with Kent Bundle

For the fusion beat the first focus identified by the focal search algorithm was the Kent bundle (FIG. 11a; see Fisher et al [29]) subsequently 3 focal areas were determined: one on the lower left septal area and two on the right ventricular wall. The estimated repolarisation times have a small dispersion (32 ms, see FIG. 11b), which is in agreement with the fact that the heart is activated from both the Kent Bundle and the His-Purkinje system.

For the beat in which the AV node was blocked a single focus was found at approximately the same location where the Kent bundle was found on the basis of the fusion beat. The resulting ECGs of both beats is shown in FIG. 12.

1.3.3 Brugada Patient

Examples of the inversely computed timing of depolarisation and repolarisation of the Brugada patient are shown in FIG. 13. These related to two time instants during the procedure: at baseline and just after the last infusion of Ajmaline. The effect of the Ajmaline on the ECG can be observed in the rms signal of the recorded BSPs (insets FIG. 13): the QRS broadened and the ST segment became slightly elevated following the administration of Ajmaline.

The first focal area was found on the left side of the septum for the baseline beat and at peak Ajmaline. For the baseline beat two additional foci were found, one on the left and one on right lateral wall (see FIG. 13*a*). The estimated activation patterns of both analysed beats are similar, although the activation times of the Ajmaline beat were later near the left and right base of the heart (FIG. 13 *a/b*).

The estimated repolarisation times of the baseline beat show a dominant epi- to endocardial recovery sequence. After the last bolus of Ajmaline, the transmural repolarisation difference in the left ventricle remained almost unchanged, though slowly shifted with time. Large differences, however, are found in the right ventricle (FIG. 13*d*). The accompanying ARIs initially show a dispersion of 116 ms increasing up to 193 ms. This expanded range is mainly caused by the very early recovery in the outflow tract area (see FIG. 13*d*). The corresponding ECGs of both beats are shown in FIG. 14.

1.3.4 Overall Performance of the Procedure

For each step in the inverse procedure the correlation and rd values are calculated between the measured ECG and the simulated ECG (see Table 2). For all subjects the resulting inverse procedure rd values were small. The initial estimates, however, showed high rd (>0.7) values despite the fact that the corresponding correlation was well above 80%.

TABLE 2

R and rd values of the 3 subjects, computed over the segments indicated, pertaining to the initial estimate (focal search) and the final solution.

| Subject | Initial activation (QRS segment only) | | Initial recovery (QRST segment) | | Activation & recovery (QRST segment) | |
|---|---|---|---|---|---|---|
| | rd | correlation | rd | correlation | rd | correlation |
| NH | 0.69 | 0.85 | 0.73 | 0.80 | 0.12 | 0.99 |
| WPW | 2.46 | 0.87 | 2.39 | 0.84 | 0.19 | 0.98 |
| | 1.72 | 0.86 | 2.39 | 0.84 | 0.17 | 0.99 |
| BG | | | | | | |
| (at 1 min) | 1.41 | 0.89 | 1.31 | 0.82 | 0.15 | 0.99 |
| (at 10 min) | 1.84 | 0.84 | 2.20 | 0.36 | 0.17 | 0.99 |

The linear slope of $\alpha(\delta)$ in the initial solution was close to −1.32 for most subjects. After optimisation the slope values decreased for all cases, except in the Brugada patient at peak Ajmaline (Table 3).

The computation time used by the inverse procedure ranged between ½ a minute (BG) up to 23 minutes (NH), depending on the number of nodes (Table 1) used in the mesh in the heart's geometry (Table 4).

TABLE 3

The range of ARI ($\alpha$), repolarisation times ($\rho$) and the slope of the linear regression between ARI and depolarisation times ($\delta$).

| Subject | (Initial) Slope mV/ms | range $\alpha$ ms | range $\rho$ ms |
|---|---|---|---|
| NH | (−1.32) −1.17 | 176-300 (124) | 275-324 (49) |
| WPW (fusion) | (−1.21) −0.83 | 168-263 (95) | 271-306 (35) |
| (AV block) | (−1.08) −0.93 | 119-268 (149) | 248-336 (88) |
| BG (at 1 min) | (−1.27) −1.12 | 182-297 (116) | 244-317 (73) |
| (at 10 min) | (−1.26) −0.92 | 108-302 (193) | 183-358 (174) |

All values shown relate to the final solution.

TABLE 4

Computation times of the focal search algorithm and the optimisation procedure.

| Subject | Focal search | | Optimisation | |
|---|---|---|---|---|
| | # scans | Computation time s | # iterations | Computation time S |
| NH | 9 | 233 | 10 | 1143 |
| WPW (fusion) | 4 | 61 | 17 | 208 |
| (AV block) | 2 | 23 | 85 | 993 |
| BG (at 1 min) | 6 | 6 | 23 | 31 |
| (at 10 min) | 1 | 1 | 36 | 46 |

Some foci in the multi-focal search were optimised more than once, resulting in more scans than foci. Within the optimisation procedure one iteration includes the optimisation of depolarisation times ($\delta$) and repolarisation times ($\rho$).

1.3.5 Amplitude Estimation of the Local Transmembrane Potential (TMP) Amplitude Based on the ST Segment of the ECG Brugada Patient Data:

For one Brugada patient ECG data were recorded during infusion of a sodium channel blocker (Ajmaline) [101], 10 bolus infusions of 10 mg, administered at one-minute intervals [102], which changes the activation and/or recovery sequence. The beats selected for analysis were: the baseline beat 5 minutes prior to infusion and the beat after the last bolus had been administered. The effect of the Ajmaline is expected, for some cases, to be rather local on the epicardium of the right outflow tract [103]. The mechanism is thought to be a structural change in this area, causing a current to load mismatch between the cardiac cells, i.e. a single cell has to activate too many neighboring cells. As a consequence the TMP amplitude drops and the propagation velocities decreases. A drop in amplitude results in an change of the ST segment level. The method proposed uses therefore only the first 40 ms (this might also longer or shorter) after the QRS complex to estimate the local TMP amplitude on the heart. Although this is a linear problem, an can therefore be solved directly through an pseudo inverse procedure, we used the Levenberg-Marquardt algorithm in an iterative procedure to determine the TMP amplitudes. This procedure is the same as used in optimizing the activation and recovery times.

The results in FIG. 15 show that this procedure identifies a small area on the epicardial outflow tract. Initially, at base line no deviation in TMP amplitude is found. After the first infusion of Ajmaline a small drop in TMP is found decreasing up to 35% at peak Ajmaline.

1.4 Discussion

For all of the three cases presented, the inversely estimated timing of activation and recovery agreed well with available physiological knowledge. The resulting ECGs closely matched the measured ECGs (rd≤0.19, correlation≥0.98, Table 2). The quality of the results and the required computation time hold promise for the application of this inverse procedure in a clinical setting.

In previous studies the required initial estimates were derived exclusively from the observed BSPs [31,53,54,55]. The robustness of these initial estimates was limited in the sense that small variations in the parameters of the first estimate lead to quite different outcomes of the inverse procedure. In the study presented here, the initial estimates are based on knowledge about the electrophysiology of the heart. The results show that this improves the quality of the inverse procedure significantly. The major elements of the inverse procedure are discussed below.

1.4.1 Activation

A first improvement in the initial estimation procedure was the incorporation of global anisotropic propagation in the simulation of ventricular activation. When using an uniform velocity the estimated activation wave revealed earlier epicardial activation for subject NH in the anterior part of the left ventricle [104]. Although no data on individual fiber orientation was available, the global handling of trans-mural anisotropy, estimated using common accepted insights [18,105,106], improved the overall performance.

A second improvement concerns the selection of foci in the multi-foci search algorithm. Within this algorithm, the correlation R between measured and simulated ECGs was used, instead of the rd values used previously. The idea to investigate the appropriateness of the correlation arose from the observation that the overall morphology of the simulated wave forms closely corresponded to the measured data, in spite of relatively high rd values. This was first observed in an application to the relatively simple atrial activation sequence, frequently involving just the "focus" in the sinus node region [85].

Subsequently, it also proved to be effective in applications to the ventricles. Each simulated activation sequence of the initial multi-foci search was scaled by an estimation of the global propagation velocity ($v_l$) derived from the QRS duration, taking into account the differences in propagation velocity in myocardial and Purkinje tissue. The QRS duration was derived from the rms(t) curve, computed from all leads referred to a zero-mean signal reference [25]. This produces the optimal estimate of the global onset and completion of the activation process.

This initial estimation procedure proved to be very insensitive to slight variations in parameters settings. This can be observed from the first subject presented, NH, yielding an initial estimate that agrees well with literature data [16,28,107]. The final activation times, resulting from the subsequently applied inverse procedure, globally resemble those of the initial activation sequence (FIG. 7a/b). Further visual inspection of the final activation sequence also showed no unphysiological phenomena.

The inverse solutions for the WPW patient have been published by Fisher et al. [29]. In their report, the solution presented solution was based an initial estimate derived from using the critical point theorem [41]. The solution for the fusion beat clearly identified the actual, invasively determined location of the accessory pathway location, but the accompanying initiation of activation at the septum and the right ventricle were not found. In our current inverse procedure, the initial estimated activation sequence of the same beat (see FIG. 11a) the accessory pathway location was identified in the first run of the multi-focal search, followed by locations from where the ventricle normally is activated [16]. The estimated activation sequence thus not only shows the correct position of the Kent bundle, but also a true fusion type of activation resulting from early activation in the right ventricle and left septum, as is to be expected in this situation. For the situation in which the AV node was blocked a single focus was found at the approximate location of the Kent bundle (see FIG. 11b).

A reduction in propagation velocity of 20-40% can be found [108] after the administration of Ajmaline, which is reflected in the estimated activation sequences before and after Ajmaline administration (compare FIGS. 13a & b).

Note that the earliest site of activation in both sequences are approximately the same. These activation patterns are similar, suggesting that the sodium channel blocker has a global influence on the propagation velocity within the heart (FIG. 13 a/b) and a more pronounced effect in the right basal area, in accordance with Linnenbank et al. [86]

1.4.2 Recovery

In previous studies only the cardiac activation times were estimated from body surface potentials [21,57]. In the current study the recovery sequence, as quantified by the timing of the steepest down slope of the local transmembrane at the heart's surface, is included as well. For the initial estimate of the ventricular recovery sequence, ρ, a quantification of the effect of electrotonic interaction on the recovery process is used, expressed by its effect on the local the activation recovery interval (ARI). Few invasive data are available on the ventricular activation recovery intervals [109]. Generally these are derived from potentials measured on the endocardial and epicardial aspects of the myocardium [40,107,110].

The linear regression slope of the $\alpha(\delta)$ curves for all 5 cases was within the range as found by Franz et al. [24] (−1.3±0.45). The estimated slopes revealed slightly smaller values in the right ventricle than those in the left ventricle and septum (FIG. 8). These results suggest that electrotonic interaction is a major determinant of the action potential duration. Consequently the ARI depends on the activation time, resulting in similar patterns for ARI and activation times. These findings are in contrast with the ARI values based on the PPS source model found by Ramathan et al. [40], in which local ARI is almost completely uncoupled from the local activation time. The differences in ARI values estimated by both methods can be attributed to the fact that the local TMP waveforms cannot be extracted uniquely from the, more global, electrograms used in the PPS based inverse procedure to extract local recovery times.

The dispersion in the recovery times found was smaller than those of the activation times, in agreement with the negative slopes observed for the $\alpha(\delta)$ function. The ranges of the activation times found were about twice as large as those of the repolarisation times for the normal cases (NH and BG (1 min), Table 3). The apex-to-base differences in the recovery times were small (20-30 ms), which is in accordance to literature data [40]. At several sites the local transmural recovery differences were more substantial (FIG. 10-13). Such large transmural recovery differences (frequently referred to by the misnomer recovery gradients), were found throughout the ventricles in all 'normal' subjects (BG baseline and NH), but not in the right ventricle of the Brugada patient (BG) after the administration of Ajmaline. It is unknown whether the recovery times of the Brugada patient match reality, but the locations having the largest deviations in recovery time do match common knowledge [87]. An explanation for the short ARI value (and the advanced activation) might lie in the fact that this area is not activated at all due to structural changes [111], an option not permitted by the presented inverse procedure.

1.4.3 Action Potential Wave Forms of the Source Model

The description of the transmembrane potential waveform used for driving the EDL source model (5), FIG. 5, proved to be adequate. When testing more refined variants only minor differences in the resulting isochrone patterns were observed, which is an indication of the robustness of the inverse procedure.

2 Inverse Procedure

To further illustrate the invention a summary of a typical procedure involving the methods according to the invention is reproduced below.

2.1 Record ECG

The inverse procedure requires the measurement of ECG signals at several (e.g. 64) locations on the body surface, a body surface map (BSM). The locations of these electrodes have to be recorded accurately to minimize modeling errors. The reference used in this for the BSM can be any reference electrode, such as the Wilson central terminal (average of the 3 extremity leads). By default the average of all signals is used as a reference. By taking the root mean square (rms) of all signals (see FIG. 16 b) the fiducial points of the P wave, QRS and T wave can be found automatically [112]. Other methods to determine the fiducial points automatically may be applied. This rms signal of the QRST sequence is used to estimate the downslopes of the repolarization phase [70]. The T wave part of the T wave is integrated and fitted by two logistic functions that are multiplied (see FIG. 17).

2.2 Volume Conductor Model Construction

The volume conductor model contains at least the geometries of the thorax, lungs, blood cavities, major blood vessels and the heart. These geometries are constructed from images, for instance MRI (see FIG. 18), CT or echo. The edges of the relevant parts are automatically detected (see FIG. 19), from which the geometry of each of the parts is reconstructed.

From these contours the geometry is obtained. Notice that the placement of the electrodes should be accurately recorded in this volume conductor model (see FIG. 20).

2.3 Electrical Heart Source Model

The used electrical source model is the Equivalent Double layer [109]. This source model is located on the surface of the heart. Currently 7 parameters are used to describe the local Transmembrane Potential (TMP), see FIG. 21. The number of parameters can be extended, such that a spike and notch are incorporated in the shape of the TMP (see section 1.3).

2.3.1 Inverse Procedure

The three ingredients described in the previous chapters are integrated in the inverse procedure. From the discretized volume conductor model a transfer matrix (A) is created, relating the currents generated in the heart ("the source") to potentials on the body surface. From the source description (S) the contribution of a part of the heart is obtained at any time instant. Multiplying both matrices results in simulated body surface potentials at any position on the thorax.

$$ECG_{sim}(t)=A \cdot S(\delta,\rho,\ldots,t)$$

Where $\delta, \rho, \ldots$ are the source parameters. The simulated ECG signals at the electrode positions of the BSM lead system are compared to the measured ECGs signals. Due to the non-linear nature of the used source model (equivalent double layer) the associated inverse problem is non-linear and requires an initial estimate for each of the used source parameters.

2.3.2 The Initial Estimate of the Depolarization and Repolarization Slopes

The initial estimate for the repolarization and a plateau slope are derived from the ECG (see section Record ECG).

2.3.3 The Initial Estimate of the Depolarization and Repolarization

The initial estimate from the depolarization moments is obtained from the fastest route algorithm, which subsequently is used to derive an initial estimate for the repolarization times. This is described in full detail in section 1.2.4 and 1.2.5.

2.3.4 The Initial Estimate of the TMP Amplitude/Resting Potential

The amplitude or resting potential is estimated from the ST segment or TP segment of the measured ECG. Due to the fact that the ECG signals are baseline corrected a drop in TMP amplitude has the same effect as a rise in resting potential. The drop in TMP amplitude might also be temporal due to a prolonged notch in the TMP as in Brugada patients (see FIG. 22). All effects are best visible when the electrical activity of the heart is minimal, i.e. the ST segment for the ventricles, and the end P wave till the beginning of the QRS complex for the atria. The associated estimation problem is nearly linear in nature, i.e. the TMP amplitude/resting potential has to be estimated from the a part of the ST segment.

The initial estimate for this problem is that the amplitude is homogeneous for the whole heart. The final result is obtained through the optimization procedure as described section 1.2.3.

2.4 Results

For the activation and recovery sequence of the ventricles see section 1.3. The activation sequence of the atria can be obtained using the same method (see FIG. 23)

The found amplitudes for an Brugada patient are also described in section 1.3.

REFERENCES

Figure 1:
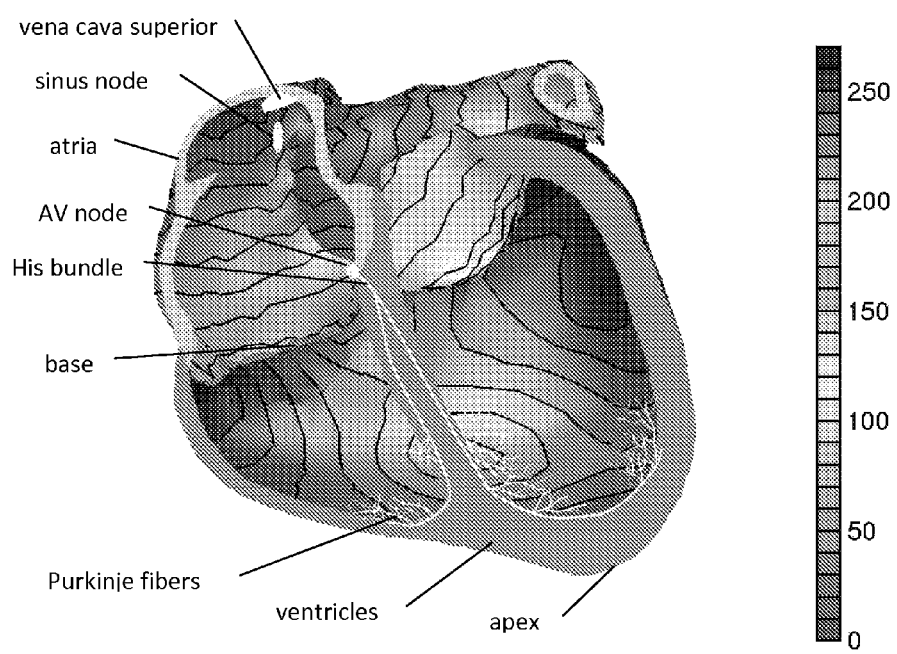
FIG. 1 Reconstruction of the heart of a healthy 22 year old male. The activation starts in the sinus node region, is delayed in the AV node (not shown). After a fast propagation of the activation along special fibers, all myocytes of the ventricle are activated. The color scale indicates the elapsed time in ms.
Figure 2:
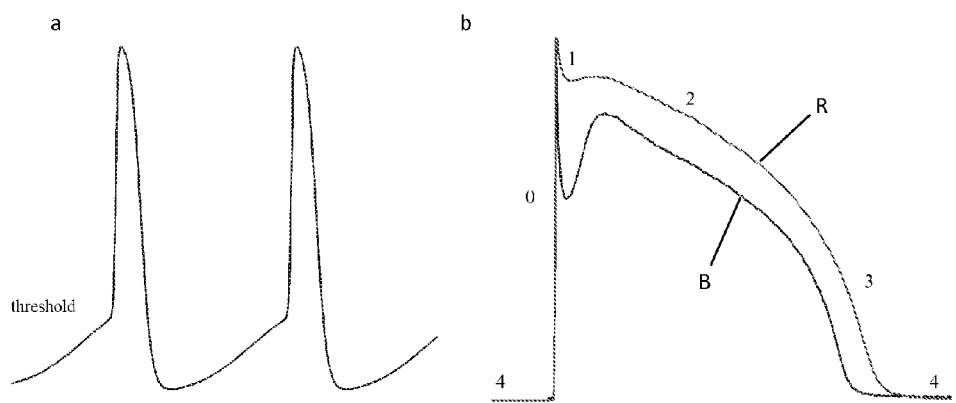
FIG. 2 Transmembrane potentials (TMP) of pacemaker cells in the sinus node (panel a), or ventricular cells (panel b). The pacemaker cells slowly but continuously depolarise until a threshold is reached (black dotted line), initiating the process of fast depolarisation. This depolarisation is immediately followed by the repolarisation, after which the whole cascade starts again. In panel b two different ventricular TMPs are shown. These TMPs are divided in 5 phases: 0) depolarisation, 1) early repolarisation, 2) plateau phase, 3) repolarisation, and 4) rest state. The red (R) waveform is commonly found in the endocardial cells whereas the blue (B) line is found in epicardial cells. The main differences are found in the early repolarisation phase.
Figure 3:
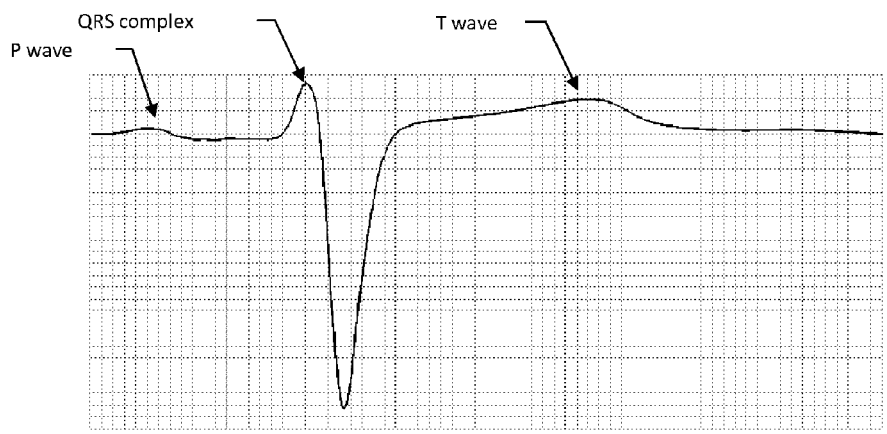
FIG. 3 An ECG signal with the P wave, (atrial activation), QRS complex (activation of the ventricles), and the T wave (recovery of the ventricles).
Figure 4:
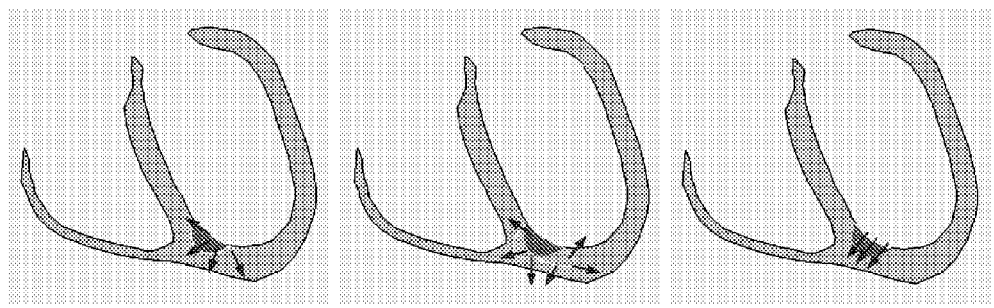
FIG. 4 Three equivalent double layers with the same solid angle, and consequently the same external potentials, e.g. on the body surface. Panel a) actual double layer at some moment during isotropic ventricular activation. Panel b) Equivalent double layer with the same solid angle but now with at an anisotropic propagating activation wave. Panel c) Equivalent double layer at the ventricular surface.
Figure 5:
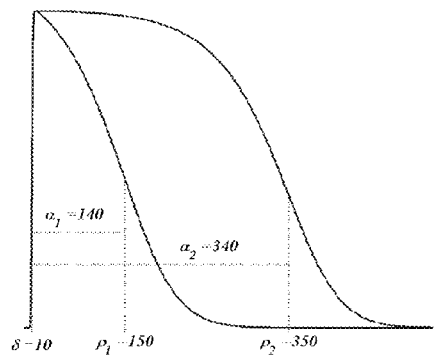
FIG. 5 Examples of TMP wave forms based on formula (5), The constants $\delta$ and $\rho$ specify two different timings of activation and recovery; the corresponding activation recovery intervals are $\alpha=\rho-\delta$.
Figure 6:
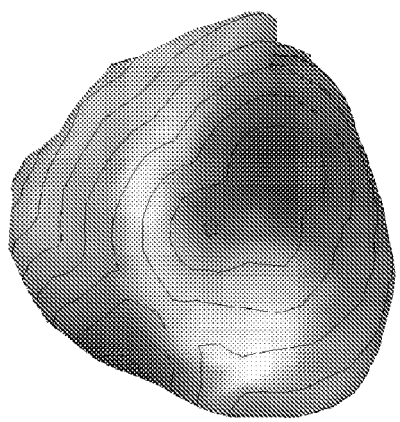
FIG. 6: Estimated activation sequences of the ventricles of a healthy subject. Panel a: the initial estimate resulting from the multi-focal search algorithm; the white dots indicate some of the foci that were identified. Panel b: the result of the subsequently applied non-linear optimisation procedure. Isochrones are drawn at 10 ms intervals. The ventricles are shown in a frontal view (left) and basal view (right).
Figure 6:
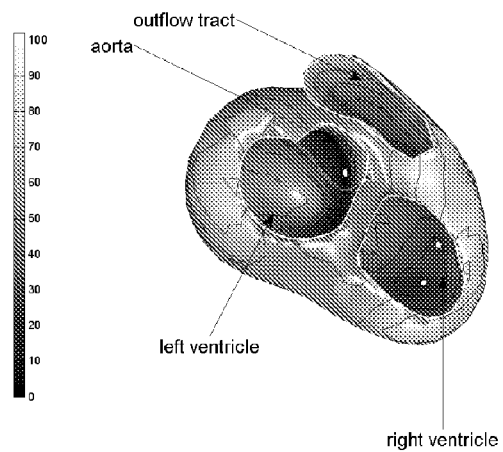
Figure 6:
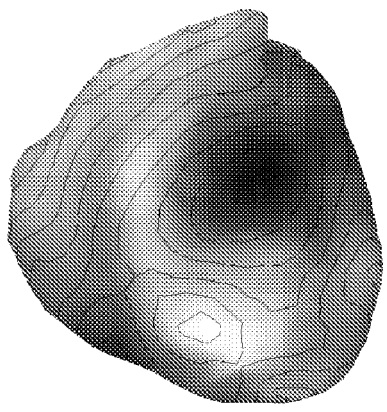
Figure 6:
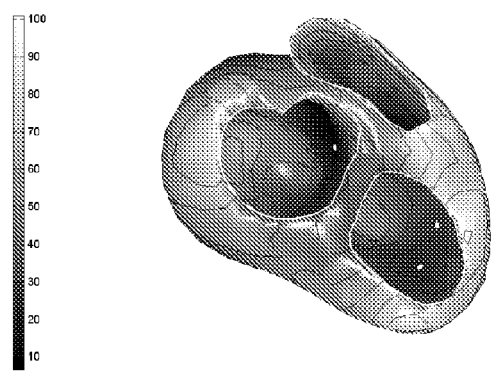
Figure 7:
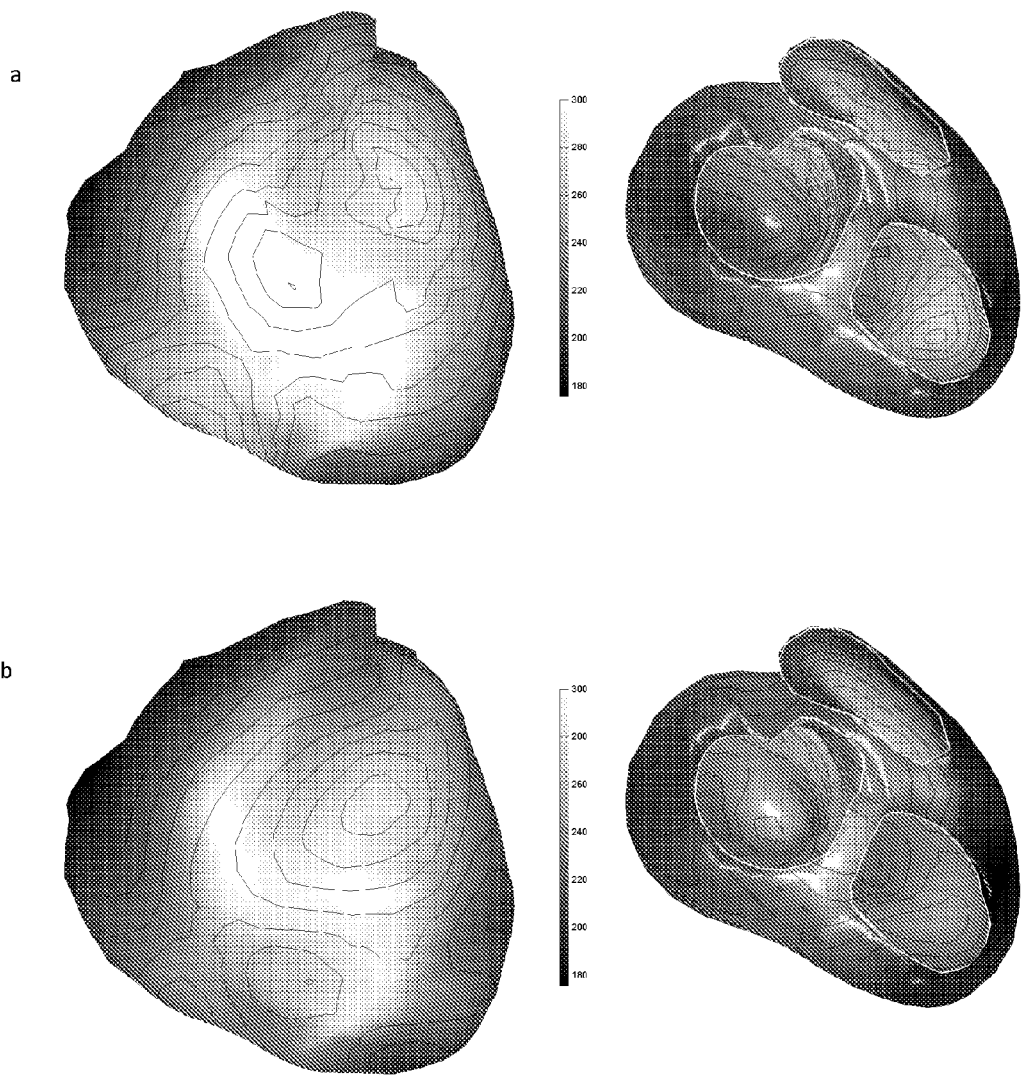
FIG. 7 Estimated activation recovery intervals at the ventricular surface of a healthy subject. Initial and final ARIs as generated in the inverse procedure. Panel a: The initial ARI estimate. Panel b: the ARI distribution after optimisation. Remaining legend as in FIG. 6.
Figure 8:
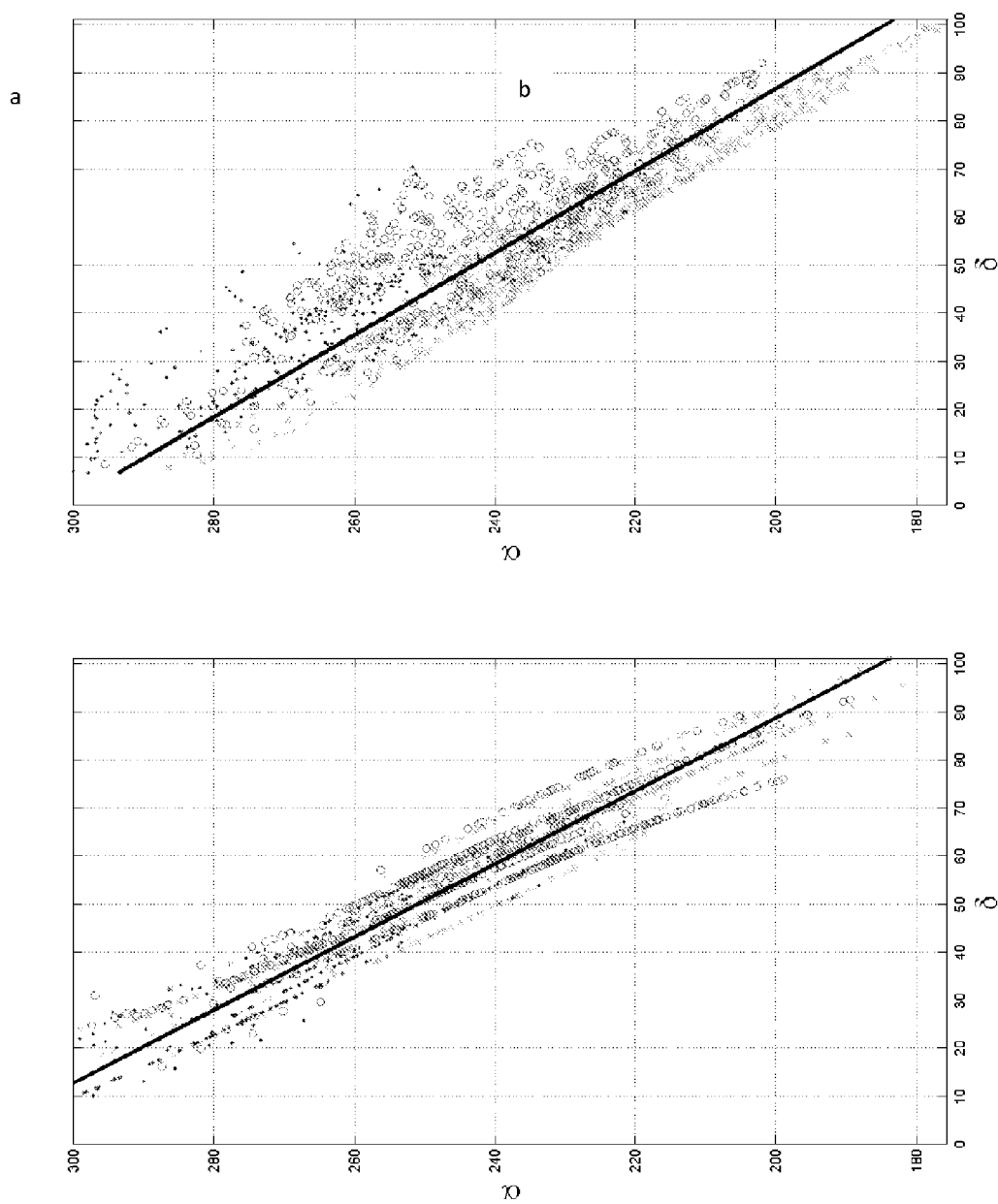
FIG. 8 Initial and final ARIs as generated in the inverse procedure. Initial estimation of the ARIs (panel a) and final estimated ARIs (panel b) as a function of the respective depolarisation sequence. The solid black line indicates the linear regression line. Three areas within the heart have been identified by different markers, right ventricle (green crosses), left ventricle (red circles) and (left and right) septum (blue dots).
Figure 9:
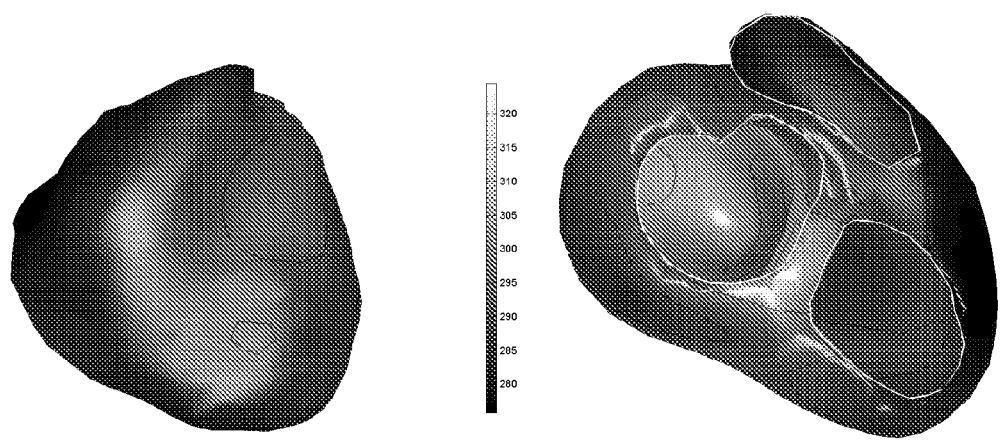
FIG. 9 Recovery sequence as obtained from the inverse procedure. Remaining legend as in FIG. 6.
Figure 10:
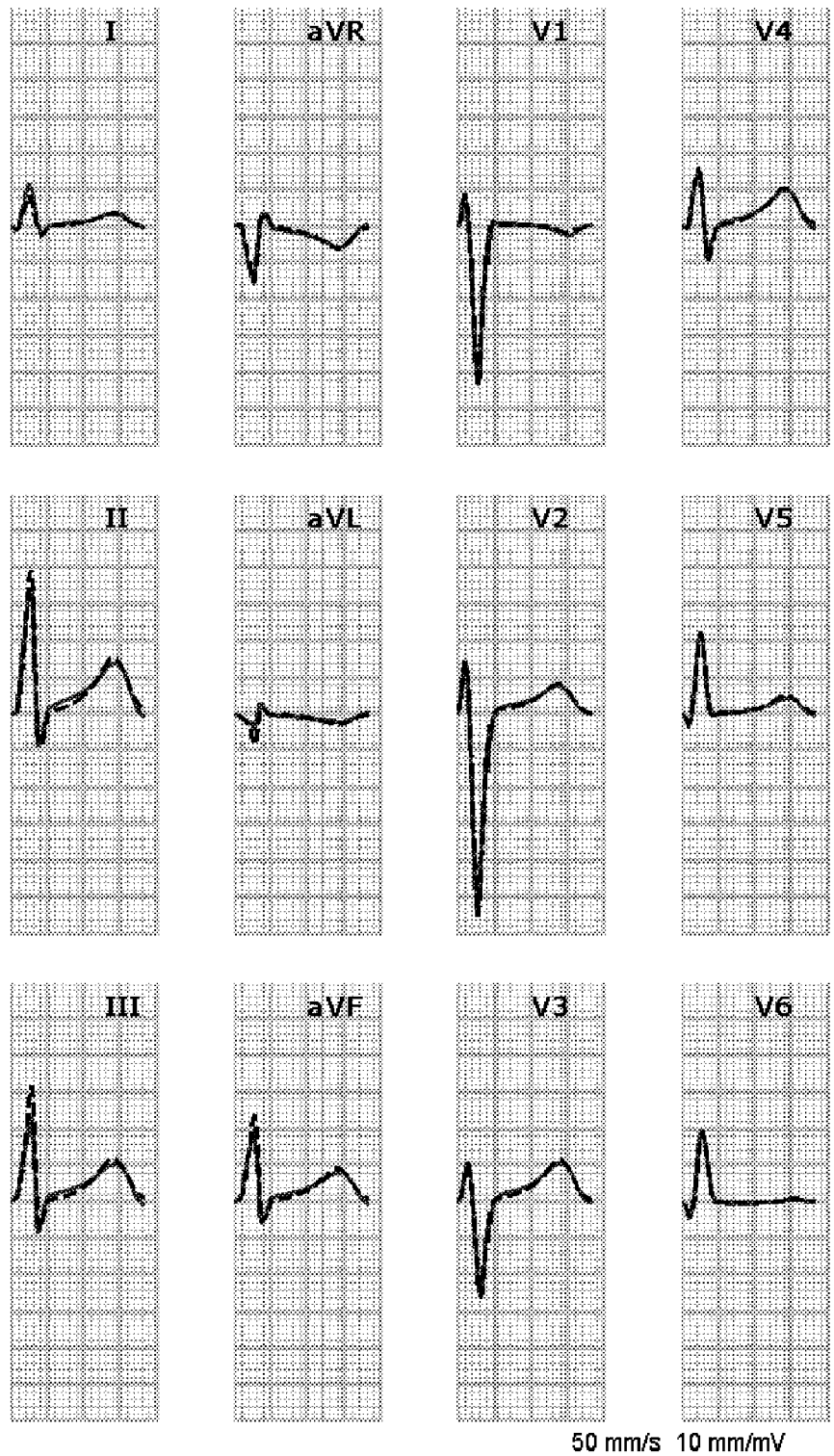
FIG. 10 Standard 12-lead ECG; in solid blue: the measured data; in dashed black: in black the simulated ECG based on the estimated activation and recovery times.
Figure 11:
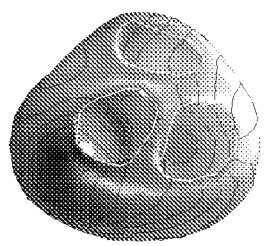
FIG. 11 The results of the inverse procedure for a fusion beat, i.e. activation initiated by a Kent bundle and the His-Purkinje system (panel a) and for a Kent-bundle-only beat (panel b). The estimated activation sequences are shown on the left, the recovery sequences on the right. The white dot indicates the position of the Kent bundle as observed invasively. Remaining legend as in FIG. 6.
Figure 11:
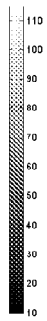
Figure 11:
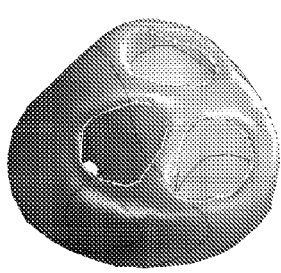
Figure 11:
Figure 11:
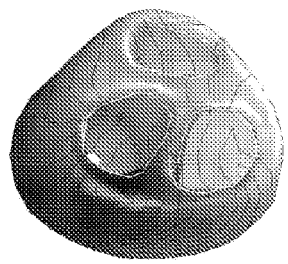
Figure 11:
Figure 11:
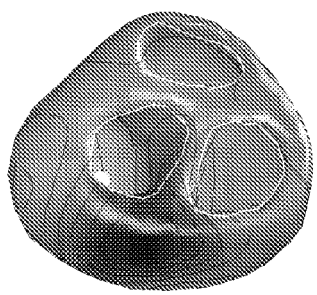
Figure 11:
Figure 12:
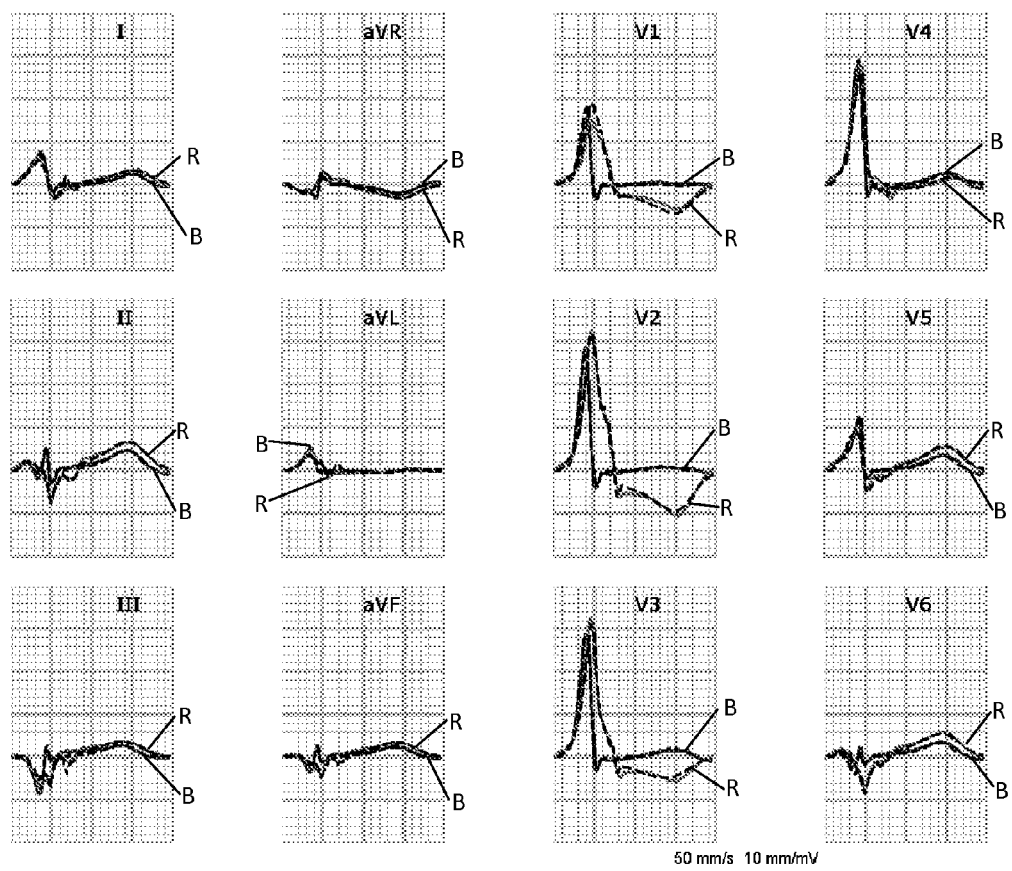
FIG. 12 The simulated (dashed black lines) and measured ECGs for a fusion beat (blue (B) lines), i.e. activation initiated by a Kent bundle and the His-Purkinje system and a beat for which the AV node was blocked by adenosine, leaving only the Kent bundle intact (red (R) lines).
Figure 13:
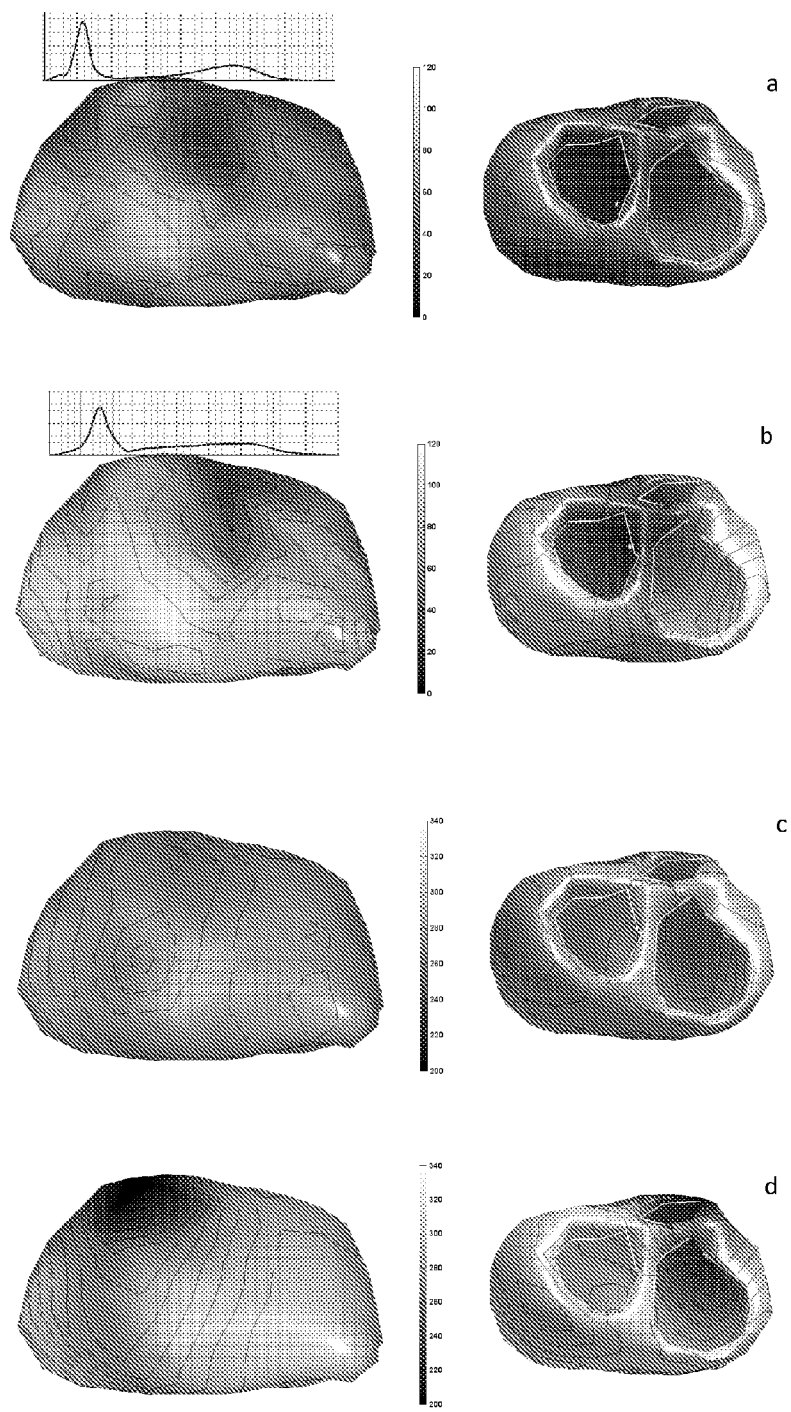
FIG. 13 Activation (panel a and b) and recovery (panel b and d) of two beats in a Brugada patient during an Ajmaline provocation test. Panel a) and c) show the activation respectively the recovery sequence estimated from the baseline ECG. Panel b) and d) show the activation respectively the recovery sequence just after the last infusion of the Ajmaline. Color scale is the same for panel a & b and panel c & d. Remaining legend see FIG. 6.
Figure 14:
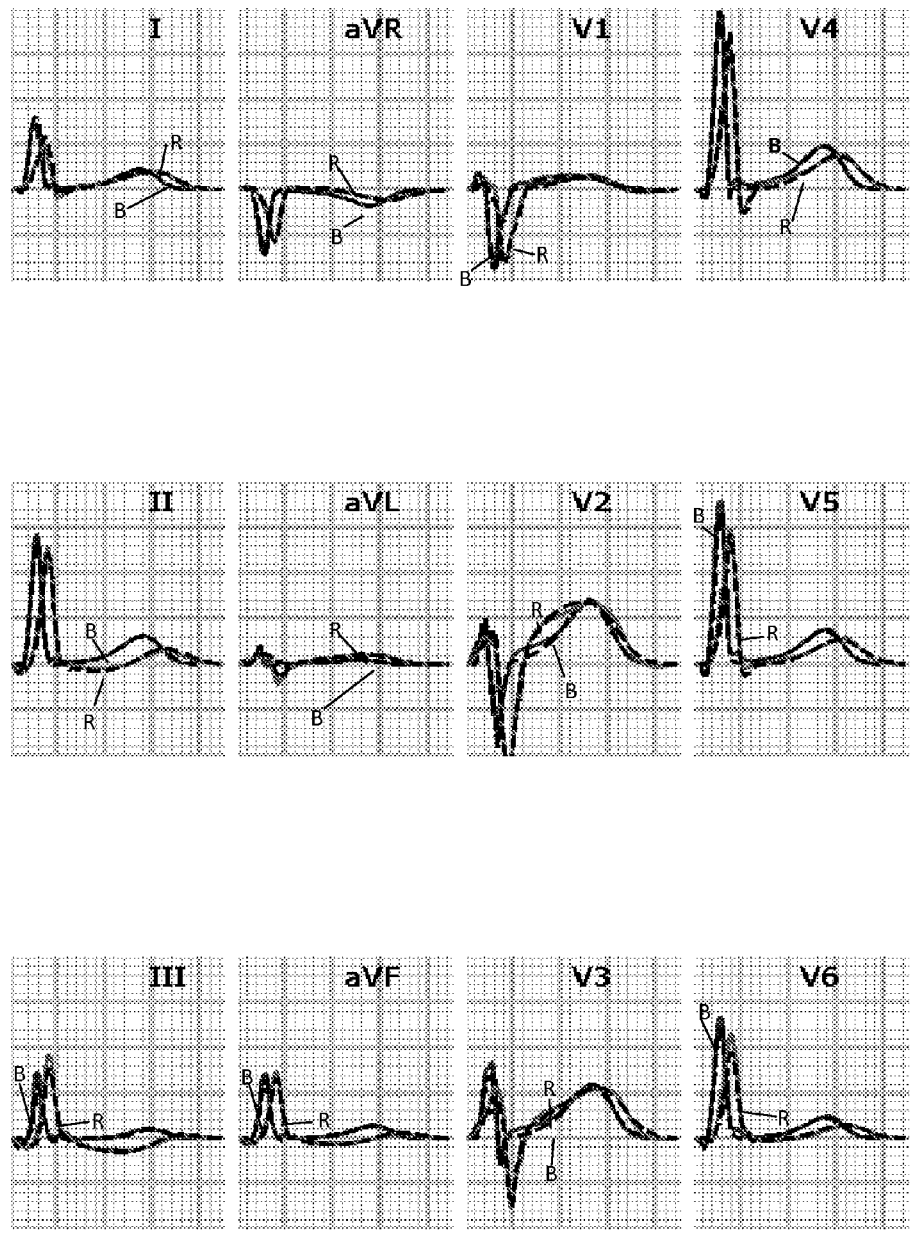
FIG. 14 The simulated (dashed black lines) and measured (blue (B) lines) ECGs for the baseline beat of the Brugada patient, and the simulated (dashed black lines) and measured (red (R) lines) ECGs of the beat at peak Ajmaline.
Figure 15:
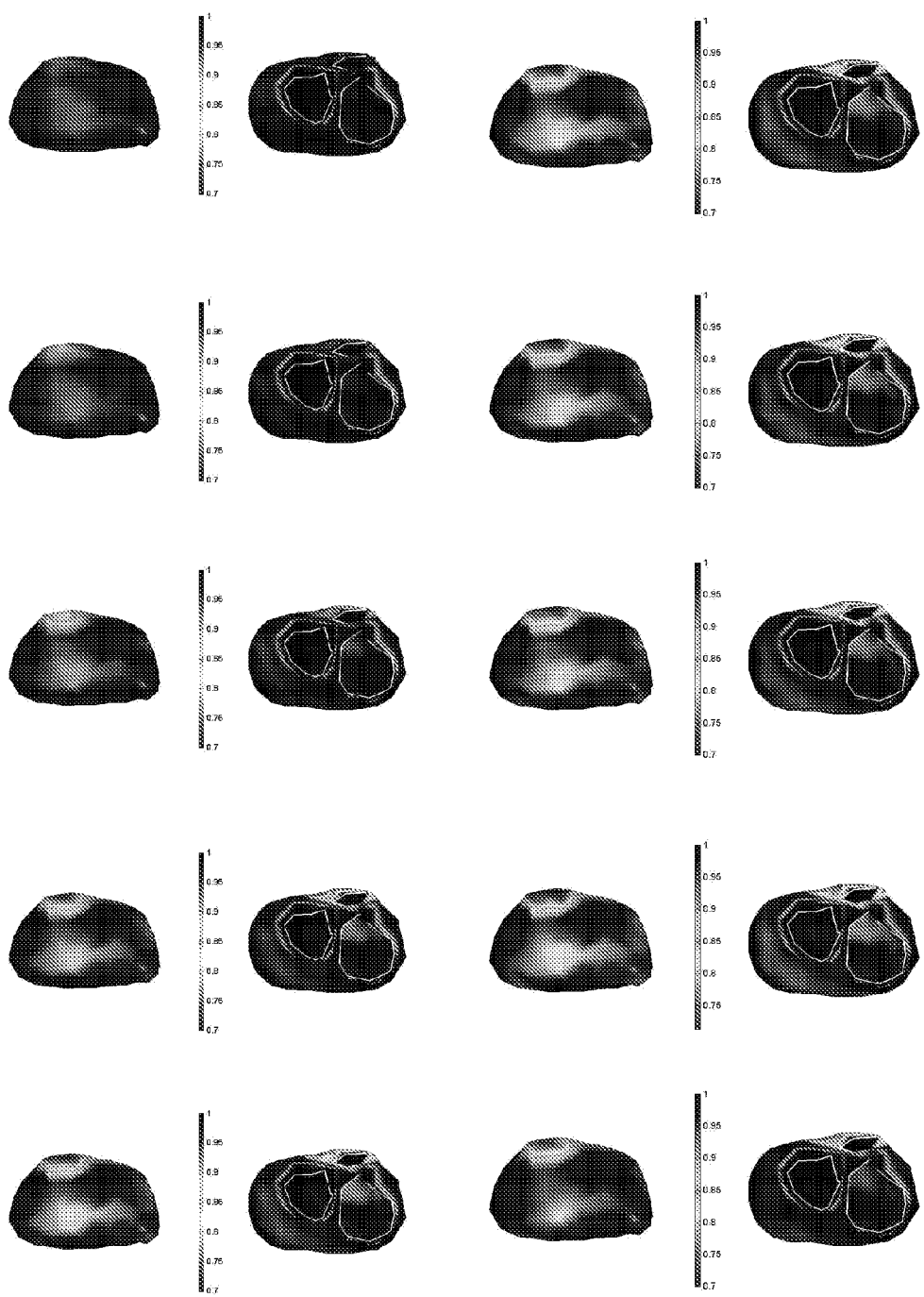
FIG. 15 The Action potential amplitude, estimated from the first 40 ms of the ST segment (starting after the J point). First 1 baseline beats top left, subsequently after the first infusion of Ajmaline every next minute. Notice the local reduction of the AP amplitude (up to 65%), in the outflow tract area (red color). The color scales on the are fixed between 0.7 and 1.
Figure 16:
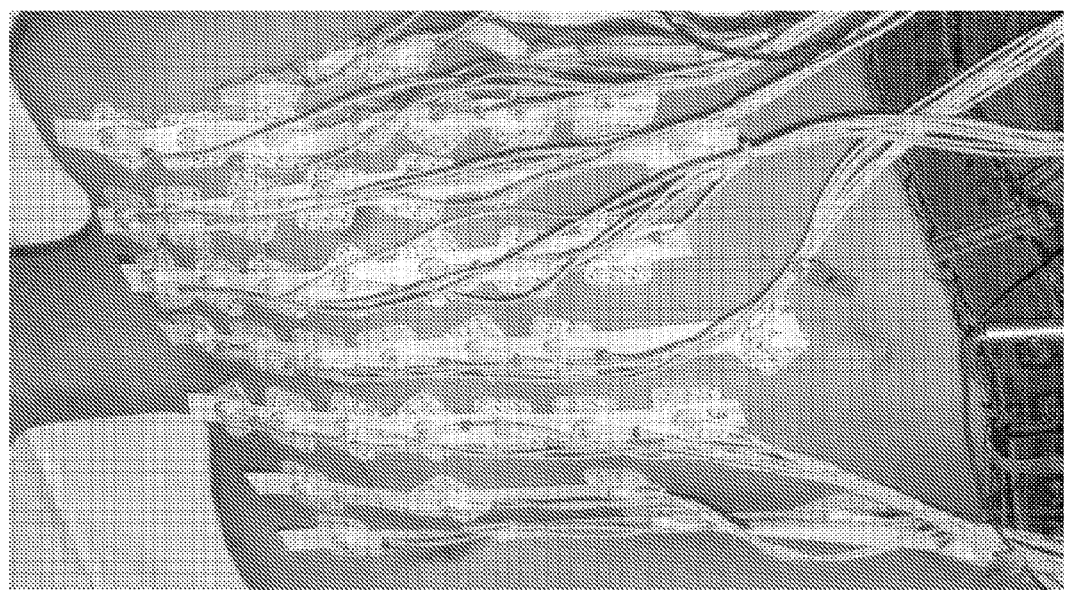
FIG. 16 Left panel: The body surface potentials recorded at 64 electrode positions and the root mean square (rms) signal (grey) on top. The fiducial points of start QRS and end T wave are indicated by a*. Right panel: Example of BSM lead system.
Figure 16:
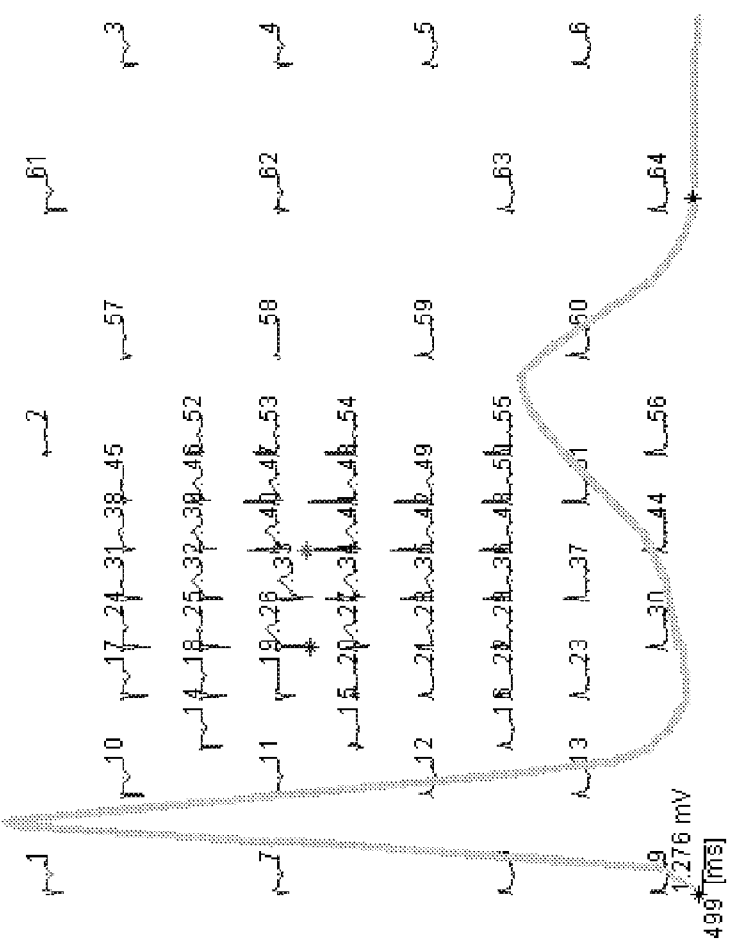
Figure 17:
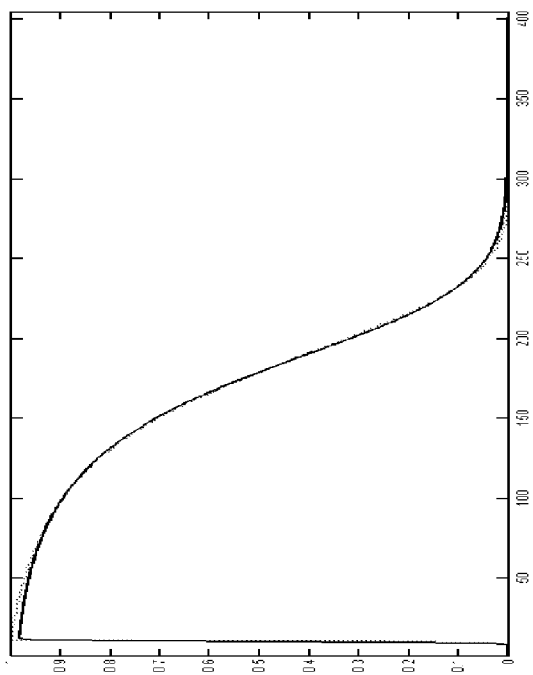
FIG. 17 Left panel: black crosses (+) indicate the fiducial points; onset QRS, end QRS, and end T wave, the dot indicates the peak of the T wave. The green line (G) is the fitted T wave by derivative of the two logistic curves. Right panel: the integral of the T wave (black) and the fitted integral curve by two logistic curve (grey line).
Figure 17:
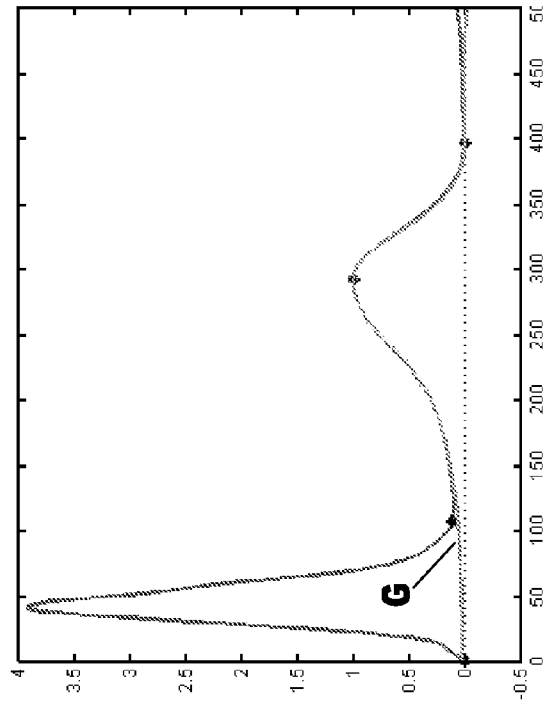
Figure 18:
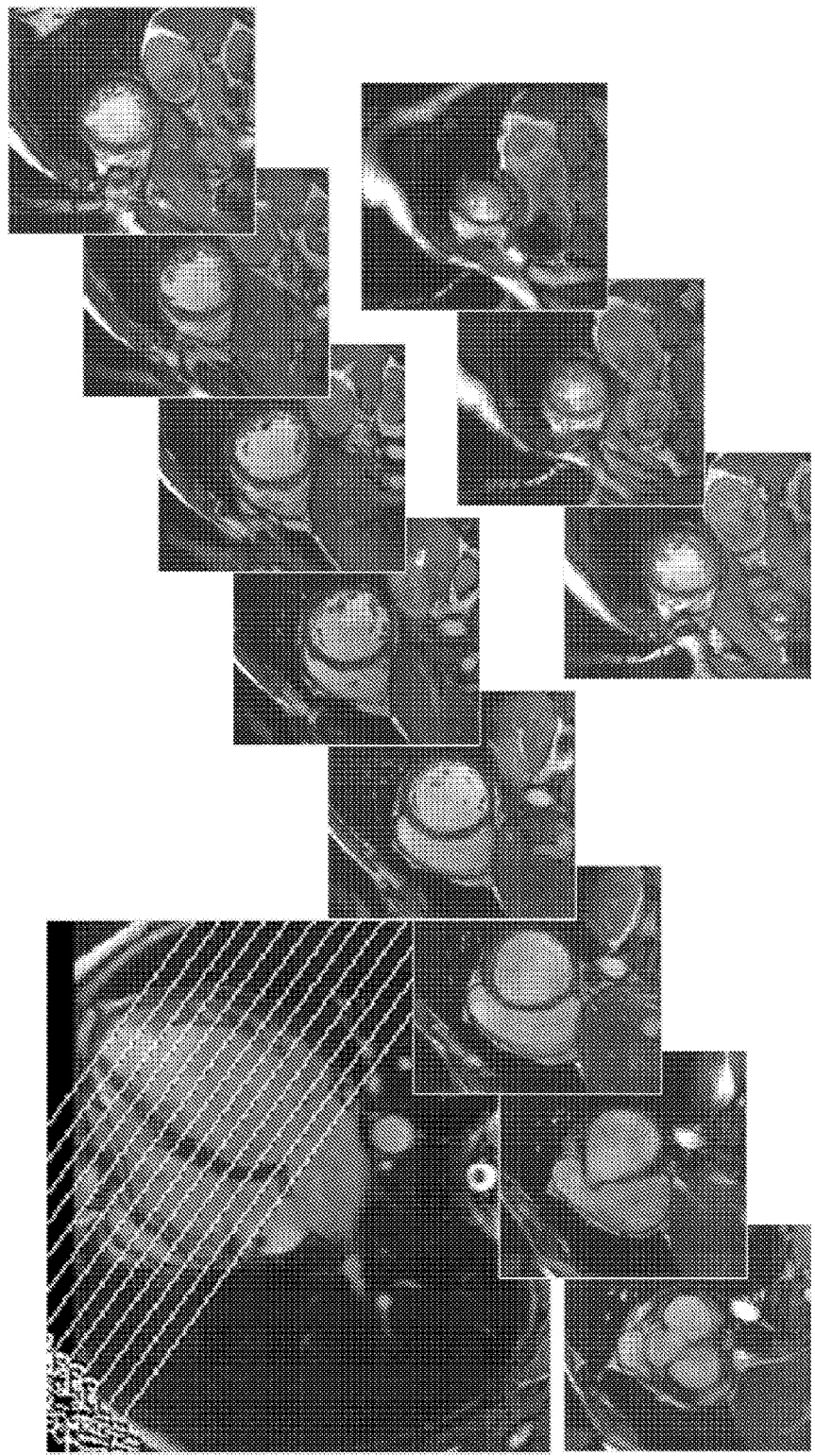
FIG. 18 Example a number of MRI images taken from a heart.
Figure 19:
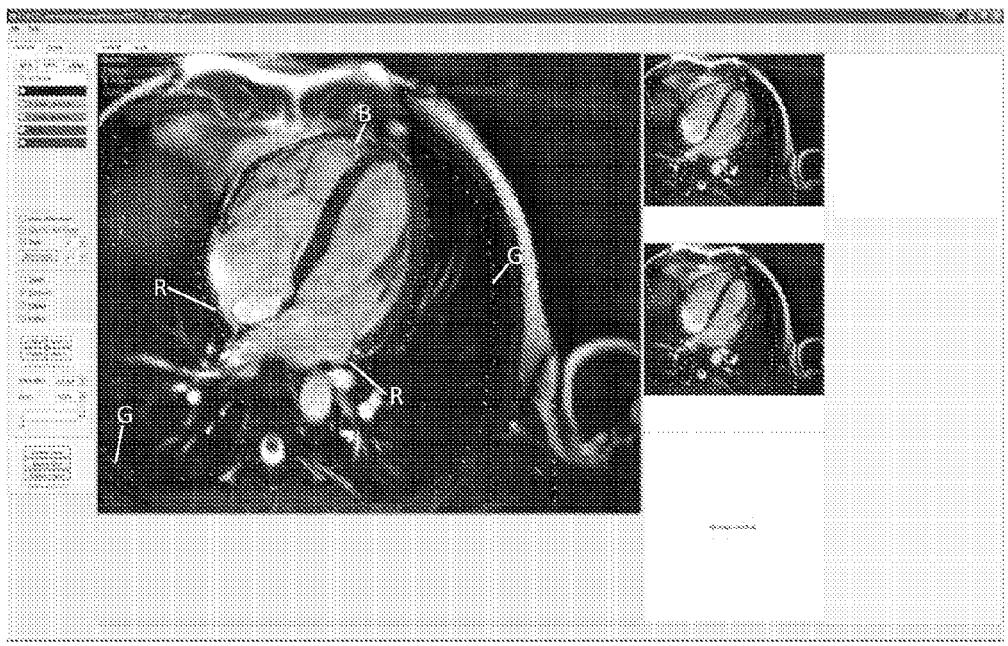
FIG. 19 Top panel: Contours drawn around the left and right ventricle, indicated by blue lines (B). Lungs are indicated by green dots (G), atria and venea cava by red dots (R). Bottom panel: all contours of the required tissues.
Figure 19:
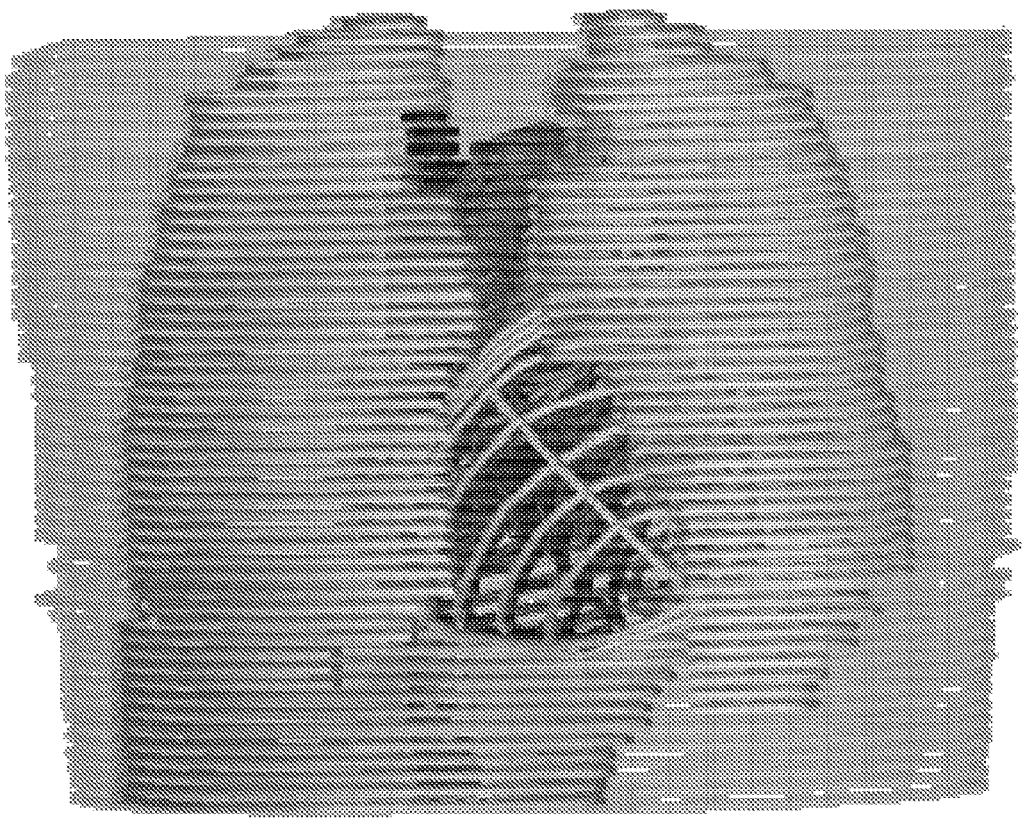
Figure 20:
FIG. 20 reconstructed thorax and heart model with the position of the electrodes
Figure 21:
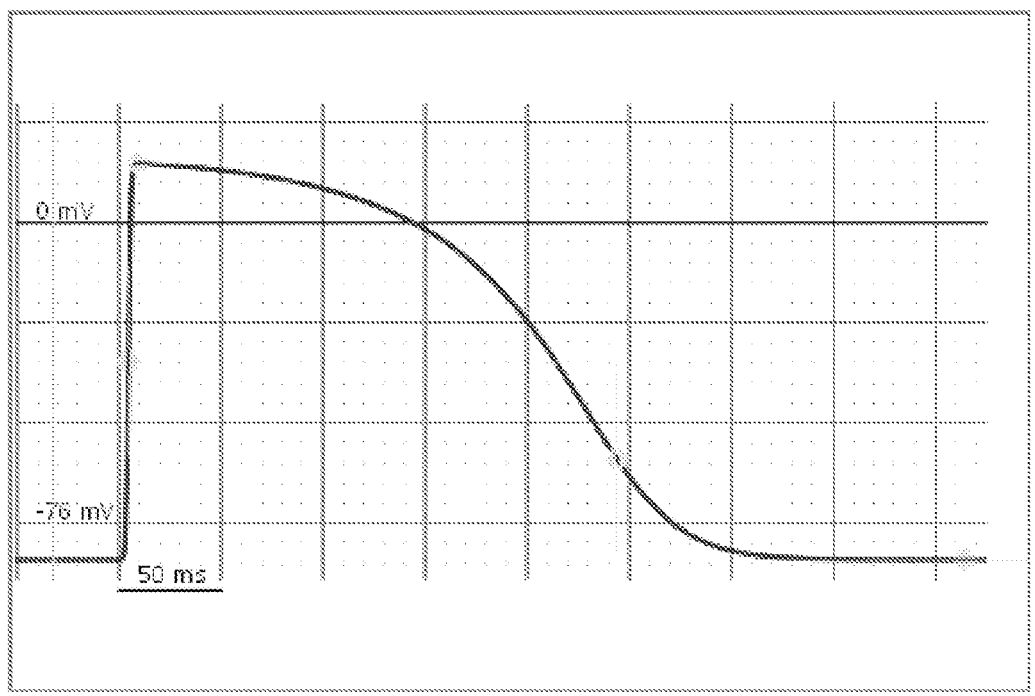
FIG. 21: TMP with the handlers in light grey. Top panel: TMP with the handlers at the depolarization moment, repolarization moment, amplitude and resting potential. Bottom panel: handlers for depolarization slope, plateau an repolarization slope.
Figure 21:
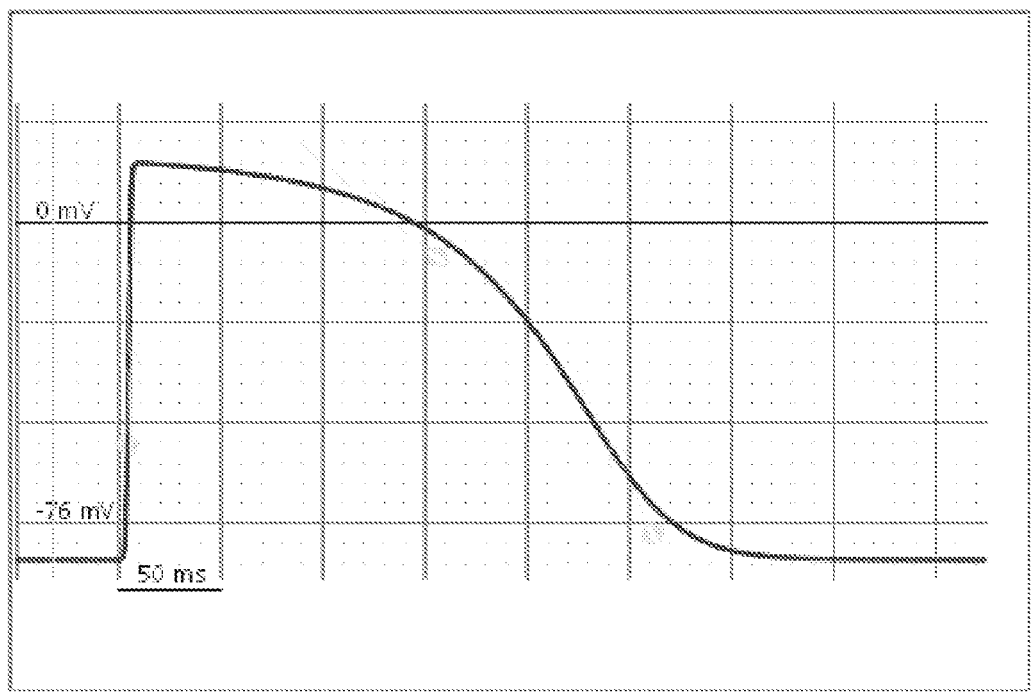
Figure 22:
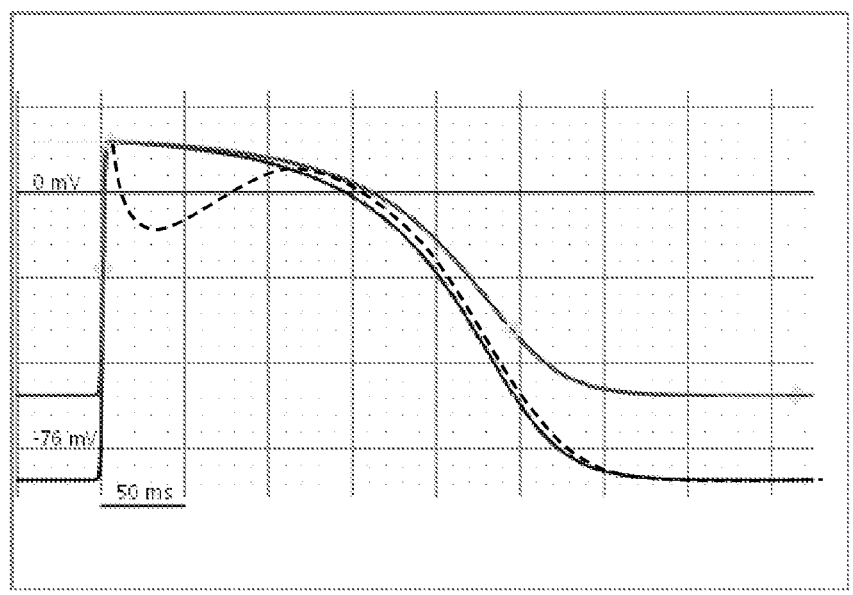
FIG. 22 Three different TMP waveforms: black normal TMP waveform without notch (endocardial node), dashed black: TMP waveform with deep and prolonged notch (associated with e.g. Brugada syndrome), Grey: TMP with a rise in TMP resting potential (associated with ischemia).
Figure 23:
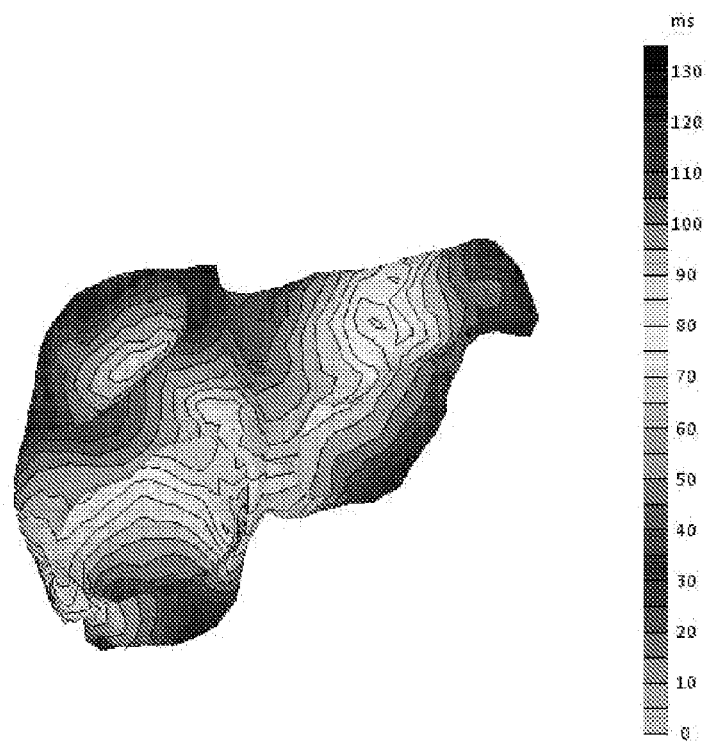
FIG. 23 Estimate of the activation sequence of the atria. Atria are in AP view.

1 Kléber, A. G. Intercellular communication and impulse propgation. Cardiac Electrophysiology From cell to bedside. D. P. Zipes and J. Jalife. Philadelphia, Saunders. 2004, 213-221.
2 Anderson, K. R., S. Y. Ho and R. H. Anderson. Location and vascular supply of sinus node in human heart. Britisch Heart Journal 41(1): 28-32, 1979
3 Kléber, A. G. and Y. Rudy. Basic Mechanisms of Cardiac Impulse Propagation and Associated Arrhythmias. Physical Review 84(2): 431-488, 2004
4 Saffitz, J. E., H. L. Kanter, K. G. Green, T. K. Tolley and E. C. Beyer. Tissue-specific determinants of anisotropic conduction velocity in canine atrial and ventricular myocardium. Circulation Research 74(6): 1065-1070, 1994
5 Roberts, D., L. Hersh and A. Scher. Influence of cardiac fiber orientation on wavefront voltage, conduction velocity, and tissue resistivity in the dog. Circulation Research 44: 701-712, 1979
6 Spach, M. S., P. C. Dolber and J. F. Heidlage. Influence of the passive anisotropic properties on directional differences in propagation following modification of the sodium conductance in human atrial muscle. Circulation Research 62: 811-832, 1988
7 Spach, M. S., W. T. Miller, P. C. Dolber, J. M. Koorsey, J. R. Sommer and C. E. Mosher. The functional role of structural complexities in the propagation of depolarization in the atrium of the dog. Circulation Research 50(2): 175-191, 1982
8 Ho, S. Y., R. H. Anderson and D. Sanchez-Quintana. Atrial structure and fibres: morphologic bases of atrial conduction. Cardiovascular Research 54(2): 325-336, 2002
9 Hansson, A., M. Holm, P. Blomstrom, R. Johansson, C. Luhrs, J. Brandt and S. B. Olsson. Right atrial free wall conduction velocity and degree of anisotropy in patients with stable sinus rhythm studied during open heart surgery. European Heart Journal 19: 293-300, 1998
10 Wang, K., S. Y. Ho, D. G. Gibson and R. H. Anderson. Architecture of atrial muscle in humans. Britisch Heart Journal 73: 559-565, 1995
11 Schuessler, R. B., T. Kawamoto, E. Dwight, M. D. Hand, M. Mitsuno, B. I. Bromberg, J. L. Cox and J. P. Boineau. Simultaneous epicardial and endocardial activation sequence mapping in the isolated canine right atrium. Circulation 88(1): 250-263, 1993
12 Anderson, R. H., S. Y. Ho and A. E. Becker. Anatomy of the human atrioventricular junctions revisited. The Anatomical Record 260(1): 81-91, 2000
13 Tawara, S. Die Topographie and Histologie der Bruckenfasern. Ein Beitrag zur Lehre von der Bedeutung der Purkinjeschen faden. Zentralb Physiol 19: 70-76, 1906

14 Demoulin, J. C. and H. E. Kulbertus. Histopathological examination of concept of left hemiblock. Britisch Heart Journal 34(8): 807-814, 1972

15 Oosthoek, P. W., S. Viragh, W. H. Lamers and A. F. Moorman. Immunohistochemical delineation of the conduction system. II: The atrioventricular node and Purkinje fibers. Circulation Research 73(3): 482-491, 1993

16 Durrer, D., R. T. van Dam, G. E. Freud, M. J. Janse, F. L. Meijler and R. C. Arzbaecher. Total excitation of the isolated human heart. Circulation 41: 899-912, 1970

17 Greenbaum, R. A., S. Y. Ho, D. G. Gibson, A. E. Becker and R. H. Anderson. Left ventricular fibre architecture in man. Britisch Heart Journal 45: 248-263, 1981

18 Streeter, D. D. J., H. M. Spotnitz, D. P. Patel, J. J. Ross and E. H. Sonnenblick. Fiber orientation in the canine left ventricle during diastole and systole. Circulation Research 24: 339-347, 1969

19 Vetter, F. J., S. B. Simons, S. Mironov, C. J. Hyatt and A. M. Pertsov. Epicardial Fiber Organization in Swine Right Ventricle and Its Impact on Propagation. Circulation Research 96(2): 244-251, 2005

20 Katz, A. M. Physiology of the heart. Philadelphia, Lippincott Williams & Wilkins, 2006

21 Burgess, M. J., L. S. Green, K. Millar, R. Wyatt and J. A. Abildskov. The sequence of normal ventricular recovery. American Heart Journal 84/5: 660-669, 1972

22 Cowan, J. C., C. J. Hilton, C. J. Griffiths, S. Tansuphaswadikul, J. P. Bourke, A. Murray and R. W. F. Campbell. Sequence of epicardial repolarization and configuration of the T wave. Britisch Heart Journal 60: 424-433, 1988

23 Millar, C. K., F. A. Kralios and R. L. Lux. Correlation between refractory periods and activation-recovery intervals from electrograms: effects of rate and adrenergic interventions. Circulation 72(6): 1372-1379, 1985

24 Franz, M. R., K. Bargheer, W. Rafflenbeul, A. Haverich and P. R. Lichtlen. Monophasic action potential mapping in a human subject with normal electrograms: direct evidence for the genesis of the T wave. Circulation 75/2: 379-386, 1987

25 Ihara, Z., A. van Oosterom and R. Hoekema. Atrial repolarization as observable during the PQ interval. Journal of Electrocardiology 39(3): 290-297, 2006

26 De Ponti, R., S. Y. Ho, J. A. Salerno-Uriarte, M. Tritto and G. Spadacini. Electroanatomic Analysis of Sinus Impulse Propagation in Normal Human Atria. J Cardiovasc Electrophysiol 13(1): 1-10, 2002

27 Hill, A. J., T. G. Laske, J. J. A. Coles, D. C. Sigg, N. D. Skadsberg, S. A. Vincent, C. L. Soule, W. J. Gallagher and P. A. Iaizzo. In Vitro Studies of Human Hearts. Annals of Thoracic Surgery 79(1): 168-177, 2005

28 Wyndham, C. R. M., T. Smith, A. Saxema, S. Engleman, R. M. Levitsky and K. M. Rosen. Epicardial activation of the intact human heart without conduction defect. Circulation 59(1): 161-168, 1979

29 Fischer, G., F. Hanser, B. Pfeifer, M. Seger, C. Hintermuller, R. Modre, B. Tilg, T. Trieb, T. Berger, F. X. Roithinger, et al. A Signal Processing Pipeline for Noninvasive Imaging of Ventricular Preexcitation. Methods of Information in Medicine 44: 588-515, 2005

30 Ghanem, R. N., P. Jia, C. Ramanathan, K. Ryu, A. Markowitz and Y. Rudy. Noninvasive Electrocardiographic Imaging (ECGI): Comparison to intraoperative mapping in patients. Heart Rhythm 2(4): 339-354, 2005

31 Huiskamp, G. J. H. and A. van Oosterom. The depolarization sequence of the human heart surface computed from measured body surface potentials. IEEE Transactions on Biomedical Engineering 35(12): 1047-1058, 1988

32 Huiskamp, G. J. M., T. F. Oostendorp, N. H. J. Pijls and A. van Oosterom. Invasive confirmation of the human ventricular activation sequence as computed from body surface potentials. Computers in Cardiology '92, Los Alamitos, IEEE Computer Society Press, 1993.

33 Einthoven, W. and K. de Lint. Ueber das normale menschliche Elektrokardiogram and Uber die capillar-elektrometrische Untersuchung einiger Herzkranken. Pflugers Arch ges Physiol 80: 139-160, 1900

34 Schalij, M. J., M. J. Janse, A. van Oosterom, v. d. W. E. E. and H. J. J. Wellens, Eds. Einthoven 2002: 100 Yeart of Electrocardiography. Leiden, The Einthoven Foundation. 2002

35 Burger, H. C. and J. B. v. Milaan. Heart Vector and Leads. Britisch Heart Journal 8: 157-161, 1946

36 Frank, E. An accurate, clinically practical system for spatial vectorcardiography. Circulation 13(5): 737-49, 1956

37 Geselowitz, D. B. Multipole Representation for an Equivalent Cardiac Generator. Proc IRE: 75-79, 1960

38 Gulrajani, R. M. The forward problem in electrocardiography. Bioelectricity and Biomagnetism. New York, John Wiley & Sons. 1998, 348-380.

39 Gulrajani, R. M. The inverse problem in electrocardiography. Bioelectricity and Biomagnetism. New York, John Wiley & Sons. 1998, 381-431.

40 Ramanathan, C., P. Jia, R. Ghanem, K. Ryu and Y. Rudy. Activation and repolarization of the normal human heart under complete physiological conditions. PNAS 103(16): 6309-6314, 2006

41 Huiskamp, G. J. M. and F. Greensite. A New Method for Myocardial Activation Imaging. IEEE Transactions on Biomedical Engineering 44(6): 433-446, 1997

42 Martin, R. O. and T. C. Pilkington. Unconstrained Inverse Electrocardiography. IEEE Transactions on Biomedical Engineering 19(4): 276-285, 1972

43 Colli-Franzone, P., L. Guerri, S. Tentonia, C. Viganotti, S. Baruffi, S. Spaggiari and B. Taccardi. A mathematical procedure for solving the inverse potential problem of electrocardiography. Analysis of the time-space accuracy from in vitro experimental data. Mathematical Biosciences 77: 353-396, 1985

44 Colli-Franzone, P. C., L. Guerri, B. Taccardi and C. Viganotti. The direct and inverse potential problems in electrocardiology. Numerical aspects of some regularization methods and application to data collected in dog heart experiments. Pavia, I. A. N.-C. N. R., 1979

45 Ghosh, S. and Y. Rudy Application of L1-Norm Regularization to Epicardial Potential Solution of the Inverse Electrocardiography Problem. Annals of Biomedical Engineering 37(5): 902-912, 2009

46 Gulrajani, R. M., P. Savard and F. A. Roberge. The inverse problem in electrocardiography: solution in terms of equivalent sources. CRC Critical Reviews in Biomed. Eng. 16: 171-214, 1988

47 Rudy, Y. and B. J. Messinger-Rapport. The Inverse Problem in Electrocardiology: Solutions in Terms of Epicardial Potentials. CRC Critical Reviews in Biomed. Eng. 16: 215-268, 1988

48 Wilson, F. N., A. G. Macleod and P. S. Barker. The Distribution of Action Currents produced by the Heart Muscle and Other Excitable Tissues immersed in Conducting Media. J Gen Physiol 16: 423-456, 1933

49 Durrer, D. and L. H. van der Tweel. Spread of activation in the left ventricular wall of the dog. American Heart Journal 46: 683-691, 1953

50 Scher, A. M., A. C. Young, A. L. Malmgren and R. R. Paton. Spread of Electrical Activity Through the Wall of the Ventricle. Cardiovascular Research 1: 539-547, 1953

51 Salu, Y. Relating the Multipole Moments of the Heart to Activated Parts of the Epicardium and Endocardium. Annals of Biomedical Engineering 6: 492-505, 1978

52 van Oosterom, A. Solidifying the Solid Angle. Journal of Electrocardiology 35S: 181-192, 2002

53 Cuppen, J. J. M. Calculating the Isochrones of Ventricular Depolarization. SIAM J Sci Stat Comp 5: 105-120, 1984

54 Modre, R., B. Tilg, G. Fischer, F. Hanser, B. Messarz and J. Segers. Atrial noninvasive activation mapping of paced rhythm data. J Cardiovasc Electrophysiol 13: 712-719, 2003

55 Roozen, H. and A. van Oosterom. Computing the activation sequence at the ventricular heart surface from body surface potentials. Medical & Biological Engineering & Computing 25: 250-260, 1987

56 Geselowitz, D. B. On the Theory of the Electrocardiogram. Proc IEEE 77/6: 857-876, 1989

57 Geselowitz, D. B. Description of cardiac sources in anisotropic cardiac muscle. Application of bidomain model. Journal of Electrocardiology 25 Sup.: 65-67, 1992

58 Huiskamp, G. J. M. Simulation of depolarization and repolarization in a membrane equations based model of the anisotropic ventricle. IEEE Transactions on Biomedical Engineering 45(7): 847-855, 1998

59 Jacquemet, V., A. van Oosterom, J. M. Vesin and L. Kappenberger. Analysis of electrocardiograms during atrial fibrillation. IEEE Eng Med Biol Mag 25(6): 79-88, 2006

60 Simms, H. D. and D. B. Geselowitz. Computation of Heart Surface Potentials Using the Surface Source Model. J Cardiovasc Electrophysiol 6: 522-531, 1995

61 van Oosterom, A. The dominant T wave and its significance. J Cardiovasc Electrophysiol 14(10 Suppl): S180-7, 2003

62 Modre, R., B. Tilg, G. Fisher and P. Wach. Noninvasive myocardial activation time imaging: a novel; inverse algorithm applied to clinical ECG mapping data. IEEE Transactions on Biomedical Engineering 49(10): 1153-1161, 2002

63 Gulrajani, R. M. The forward problem in electrocardiography. Bioelectricity and Biomagnetism. New York, John Wiley & Sons. 1998, 348-380.

64 Berger, T., G. Fischer, B. Pfeifer, R. Modre, F. Hanser, T. Trieb, F. X. Roithinger, M. Stuehlinger, O. Pachinger, B. Tilg, et al. Single-Beat Noninvasive Imaging of Cardiac Electrophysiology of Ventricular Pre-Excitation. J Am Coll Cardiol: 2045-52, 2006

65 Cuffin, B. N. and D. Geselowitz. Studies on the electrocardiogram using realistic cardiac and torso models. IEEE Transactions on Biomedical Engineering 24(3): 242-252, 1977

66 Huiskamp, G. J. M. and A. van Oosterom. Tailored versus realistic geometry in the inverse problem of electrocardiography. IEEE Transactions on Biomedical Engineering 36: 827-835, 1989

67 van Oosterom, A. and T. F. Oostendorp. ECGSIM: an interactive tool for studying the genesis of QRST waveforms. Heart 90(2): 165-168, 2004

68 van Oosterom, A. and G. J. M. Huiskamp. The effect of torso inhomogeneities on body surface potentials quantified by using tailored geometry. Journal of Electrocardiology 22: 53-72, 1989

69 Rudy, Y. and J. E. Burns. Noninvasive Electrocardiographic Imaging. Ann. Noninv. Electrocardiol. 4: 340-359, 1999

70 van Oosterom, A. Genesis of the T wave as based on an equivalent surface source model. Journal of Electrocardiography 34(Supplement 2001): 217-227, 2001

71 van Oosterom, A. and V. Jacquemet. Genesis of the P wave: Atrial signals as generated by the equivalent double layer source model. Europace 7(s2): S21-29, 2005

72 van Oosterom, A. and V. Jacquemet. A Parameterized Description of Transmembrane Potentials used in Forward and Inverse Procedures. Int Conf Electrocardiol, Gdansk; Poland, Folia Cardiologica, 2005.

73 Huiskamp, G. J. M. and A. van Oosterom. The depolarization sequence of the human heart surface computed from measured body surface potentials. IEEE Transactions on Biomedical Engineering 35(12): 1047-1058, 1988

74 Greensite, F. Remote reconstruction of confined wavefront propagation. Inverse Problems 11: 361-370, 1995

75 Colli-Franzone, P. and L. Guerri. Mathematical Model of the Exitation Process in Myocardial Tissue: Influence of Fiber Rotation on Wavefront Propagation and Potential Field. Mathematical Biosciences 101: 155-235, 1990

76 Henriquez, A. P., R. Vogel, B. J. Muller-Borer, C. S. Henriquez, R. Weingart and W. E. Cascio. Influence of dynamic gap junction resistance on impulse propagation in ventricular myocardium: a computer simulation study. Biophysical Journal 81(4): 2112-21, 2001

77 Potse, M., B. Dube, J. Richer, A. Vinet and R. M. Gulrajani. A comparison of monodomain and bidomain reaction-diffusion models for action potential propagation in the human heart. IEEE Transactions on Biomedical Engineering 53(12): 2425-2435, 2006

78 Rudy, Y. and W. L. Quan. A model study of the effects of the discrete cellular structure on electrical propagation in cardiac tissue. Circulation Research 61: 815-823, 1987

79 Siregar, P., J. P. Sinteff, N. Julen and P. Le Beux. An Interactive 3D Anisotropic Cellular Automata Model of the Heart. Computers and Biomedical Research 31(5): 323-347, 1998

80 Werner, C. D., F. B. Sachse and O. Dossel. Electrical excitation propagation in the human heart. International Journal of Bioelectromagnetism 2(2), 2000

81 Sermesant, M., E. Konukoğlu, H. Delingette, Y. Coudière, P. Chinchapatnam, K. Rhode, R. Razavi and N. Ayache. An Anisotropic Multi-front Fast Marching Method for Real-Time Simulation of Cardiac Electrophysiology. Functional Imaging and Modeling of the Heart. 2007, 160-169.

82 Sethian, J. A. A fast marching level set method for monotonically advancing fronts. Proceedings of the National Academy of Sciences 93(4): 1591-1595, 1996

83 Dijkstra, E. W. A Note on Two Problems in Connection with Graphs. Numerische Mathematik 1: 269-271, 1959

84 van Dam, P. M. and A. van Oosterom. Volume conductor effects involved in the genesis of the P wave. Europace 7: S30-S38, 2005

85 van Dam, P. M. and A. van Oosterom. Atrial Excitation Assuming Uniform Propagation. Journal of Cardiovascular Electrophysiology 14(s10): S166-S171, 2003

86 Linnenbank, A. C., A. van Oosterom, T. F. Oostendorp, P. van Dessel, A. C. Van Rossum, R. Coronel, H. L. Tan and J. M. De Bakker. Non-invasive imaging of activation times during drug-induced conduction changes. World Congress on Medical Physics and Biomedical Engineering, IFMBE, Seoul, 2006.

87 Wolpert, C., C. Echternach, C. Veltmann, C. Antzelevitch, G. P. Thomas, S. Spehl, F. Streitner, J. Kuschyk, R. Schimpf, K. K. Haase, et al. Intravenous drug challenge using flecainide and ajmaline in patients with Brugada syndrome. Heart rhythm 2(3): 254-260, 2005

88 Haws, C. W. and R. L. Lux. Correlation Between In Vivo Transmembrane Action Potential Durations and Activation-Recovery Intervals From Electrograms. Circulation 81(1): 281-288, 1990

89 van Oosterom, A. The Singular Value Decomposition of the T wave: Its Link with a Biophysical Model of Repolarization. Int. J. Bioelectromagnetism 4: 59-60, 2002

90 van Oosterom, A., Ed. Electrocardiography. The Biophysics of Heart and Circulation. Bristol, Inst of Physics Publ.1993

91 Marquardt, D. W. An algorithm for least-squares estimation of non-linear parameters. J. Soc. Indust. Appl. Math. 11(2): 431-441, 1963

92 Huiskamp, G. J. M. Difference formulas for the surface Laplacian on a triangulated surface. Journal of Computational Physics 95(2): 477-496, 1991

93 van Dam, R. T. and M. J. Janse. Activation of the heart. Comprehensive Electrocardiology. P. W. Macfarlane and T. T. V. Lawrie. Oxford, Pergamon Press. 1989.

94 Wilson, R. J. Introduction to graph theory. London, Longman, 1975

95 van Oosterom, A. and P. M. van Dam. The intra-myocardial distance function as used in the inverse computation of the timing of depolarization and repolarization. Computers in Cardiology Lyon, France, IEEE Computer Society Press, 2005.

96 Brody, D. A. A theoretical analysis of intracavitary blood mass influence on the heart-lead relationship. Circulation Research IV: 731-738, 1956

97 Sano, T., N. Takayama and T. Shimamoto. Directional Differences of Conduction Velocity in the Cardiac Ventricular Syncytium Studied by Microelectrodes. Circulation Research VII: 262-267, 1959

98 Spach, M. S. and P. C. Dolber. Relating extracellular potentials and their derivatives to anisotropic propagation at a microscopic level in human cardiac muscle. Evidence for electrical uncoupling of side-to-side fiber connections with increasing age. Circulation Research 58(3): 356-71, 1986

99 van Oosterom, A. and V. Jacquemet. The effect of tissue geometry on the activation recovery interval of atrial myocytes. Physica D: Nonlinear Phenomena 238(11-12): The effect of tissue geometry on the activation recovery interval of atrial myocytes, 2009

100 van Oosterom, A. The dominant T wave. Journal of Electrocardiology 37 Suppl: 193-7, 2004

101 Linnenbank, A. C., A. van Oosterom, T. F. Oostendorp, P. van Dessel, A. C. Van Rossum, R. Coronel, H. L. Tan and J. M. De Bakker. Non-invasive imaging of activation times during drug-induced conduction changes. World Congress on Medical Physics and Biomedical Engineering, IFMBE, Seoul, 2006.

102 Wolpert, C., C. Echternach, C. Veltmann, C. Antzelevitch, G. P. Thomas, S. Spehl, F. Streitner, J. Kuschyk, R. Schimpf, K. K. Haase, et al. Intravenous drug challenge using flecainide and ajmaline in patients with Brugada syndrome. Heart rhythm 2(3): 254-260, 2005

103 Coronel, R., S. Casini, T. T. Koopmann, F. J. G. Wilms-Schopman, A. O. Verkerk, J. R. de Groot, Z. Bhuiyan, C. R. Bezzina, M. W. Veldkamp, A. C. Linnenbank, et al. Right Ventricular Fibrosis and Conduction Delay in a Patient With Clinical Signs of Brugada Syndrome: A Combined Electrophysiological, Genetic, Histopathologic, and Computational Study. Circulation 112(18): 2769-2777, 2005

104 van Dam, P., T. Oostendorp and A. van Oosterom. Application of the fastest route algorithm in the interactive simulation of the effect of local ischemia on the ECG. Medical & Biological Engineering & Computing 47(1): 11-20, 2009

105 Spach, M. S., W. T. Miller, E. Miller-Jones, R. B. Warren and R. C. Barr. Extracellular potentials related to intracellular action potentials during impulse conduction in anisotropic canine cardiac muscle. Circulation Research 45: 188-204, 1979

106 Wang, Y. and Y. Rudy. Action potential propagation in inhomogeneous cardiac tissue: safety factor considerations and ionic mechanism. Am J Physiol Heart Circ Physiol 278: H1019-29, 2000

107 Janse, M. J., E. A. Sosunov, R. Coronel, T. Opthof, E. P. Anyukhovsky, J. M. T. de Bakker, A. N. Plotnikov, I. N. Shlapakova, P. Danilo, Jr., J. G. P. Tijssen, et al. Repolarization Gradients in the Canine Left Ventricle Before and After Induction of Short-Term Cardiac Memory. Circulation 112(12): 1711-1718, 2005

108 Romero Legarreta, I., S. Bauer, R. Weber dos Santos, H. Koch and M. Bär. Spatial Properties and Effects of Ajmaline for Epicardial Propagation on Isolated Rabbit Hearts: Measurements and a Computer Study. Computers in Cardiology Durham, N.C., USA, 2007.

109 van Oosterom, A. The Equivalent Surface Source Model in its Application to the T Wave. Electrocardiology '01, Univ Press São Paolo, 2002.

110 Ghanem, R. N., J. E. Burnes, A. L. Waldo and Y. Rudy. Imaging Dispersion of Myocardial Repolarization, II: Noninvasive Reconstruction of Epicardial Measures. Circulation 104(11): 1306-1312, 2001

111 Wilde, A. A. M. and C. Antzelevitch. The continuing story: The aetiology of Brugada syndrome: functional or structural basis? European Heart J 24(22): 2073-a-, 2003112

112 Barbaro, V., P. Bartolini and M. Fierli. New algorithm for the detection of the ECG fiducial point in the averaging technique. Medical and Biological Engineering and Computing 29(2): 129-135, 1991

The invention claimed is:

1. A method for providing a representation of the distribution, fluctuation and/or movement of electrical activity through heart tissue, said method comprising:
    obtaining an ECG of the heart comprising said tissue;
    obtaining a model of the heart geometry;
    obtaining a model of the torso geometry;
    relating the measurements per electrode of the ECG to the heart and torso geometry and estimating the distribution, fluctuation and/or movement of electrical activity through heart tissue based upon an electrical heat source model wherein an initial estimate of activation is based upon a fastest route algorithm, shortest path algorithm and/or fast marching algorithm.

2. The method according to claim 1, whereby the representation is an estimation of the activation of different areas of the heart.

3. The method according to claim 1, whereby the heart- and/or the torso geometry is based upon a measurement by MRI.

4. The method according to claim 1, whereby repolarisation (recovery) of areas of the heart muscle is estimated based upon the sequence of activation through the heart.

5. The method according to claim 4, further comprising adjusting the activation estimation by estimating the fiber orientation in at least one area of the heart muscle.

6. The method according to claim 4, further comprising adjusting the recovery estimation by estimating the fiber orientation in at least one area of the heart muscle.

7. The method according to claim 4, whereby the speed, activation or recovery estimation is optimised by a Levenberg-Marquardt method.

8. The method according to claim 1, wherein an equivalent double layer model is used as an electrical source model.

9. The method according to claim 1, wherein the amplitude of a local transmembrane potential in a heart muscle is estimated based on the ST segment of an ECG of said heart muscle.

10. The method according to claim 1, wherein a volume conductor model of the heart and/or torso geometry is adjusted based upon a database of various heart and/or torso geometries.

11. The method according to claim 1, wherein a source model of the heart is adjusted based upon a database of various heart geometries.

12. The method according to claim 1, wherein the initial estimate of activation includes a multi-foci search for identifying an activation sequence.

13. A method for determining the effects of a substance on at least one area of a heart muscle, comprising
    obtaining a first and at least one further representation of a heart muscle by performing steps further comprising
    obtaining an ECG of the heart comprising said tissue,
    obtaining a model of the heart geometry,
    obtaining a model of the torso geometry, and
    relating the measurements per electrode of the ECG to the heart and torso geometry and estimating the distribution, fluctuation and/or movement of electrical activity through heart tissue based upon an electrical heart source model wherein an initial estimate of activation is based upon a fastest route algorithm, shortest path algorithm and/or fast marching algorithm;
    whereby said first representation is obtained from a heart not exposed to said substance and said at least one further representation is obtained during and/or after exposure of said heart to said substance.

14. The method according to claim 13, wherein said first and further representations are obtained through continuous measurements.

15. The method according to claim 13, whereby said substance is at least one medicine intended to treat heart disease.

16. The method according to claim 13 wherein said substance is at least one medicine to be tested for side effects on the heart muscle.

17. The method according to claim 13 whereby different areas of a heart muscle are analyzed for effects of said substance.

18. The method according to claim 13, further comprising providing consecutive representations of the movement of electrical activity through said heart muscle.

19. The method according to claim 18 whereby said representations are obtained by continuous measurements.

20. The method according to claim 13, further comprising comparing at least one representation of the movement of electrical activity through a heart muscle with at least one reference representation from a database.

21. The method according to claim 13, whereby speed of activation through the heart muscle is estimated based upon the estimated activation and the estimated fiber orientation.

22. The method according to claim 13, wherein the initial estimate of activation includes a multi-foci search for identifying an activation sequence.

\* \* \* \* \*